(12) United States Patent
Ho et al.

(10) Patent No.: US 10,036,033 B2
(45) Date of Patent: Jul. 31, 2018

(54) METHOD OF INHIBITING SPROUTING IN PLANT TISSUES

(71) Applicant: Academia Sinica, Taipei (TW)

(72) Inventors: Tuan-Hua David Ho, Taipei (TW); Wan-chi Lin, Taipei (TW); Kuan-Ying Huang, Taipei (TW)

(73) Assignee: Academia Sinica, Taipei (TW)

( * ) Notice: Subject to any disclaimer, the term of this patent is extended or adjusted under 35 U.S.C. 154(b) by 22 days.

(21) Appl. No.: 14/828,842

(22) Filed: Aug. 18, 2015

(65) Prior Publication Data

US 2016/0177329 A1    Jun. 23, 2016

Related U.S. Application Data

(60) Provisional application No. 62/038,621, filed on Aug. 18, 2014.

(51) Int. Cl.
*C12N 15/87* (2006.01)
*C12N 15/82* (2006.01)

(52) U.S. Cl.
CPC ................ *C12N 15/8267* (2013.01)

(58) Field of Classification Search
None
See application file for complete search history.

(56) References Cited

PUBLICATIONS

Jeong-Hwan et al (2005, Plant Molecular Biology 58(6):823-838).*
Bowie et al, Science 247:1306-1310, 1990.*
McConnell et al, Nature 411 (6838):709-713, 2001.*
Jeong-Hwan et al (2005, Plant Molecular Biology 58(6): 823-838).*

* cited by examiner

*Primary Examiner* — Stuart F Baum
(74) *Attorney, Agent, or Firm* — Wolf, Greenfield & Sacks, P.C.

(57) ABSTRACT

The present invention relates to a method for inhibiting sprouting, particularly pre-harvest sprouting, in plant seeds, by introducing a polynucleotide encoding a FCA protein into the plant.

10 Claims, 10 Drawing Sheets

A

Reporter construct:

METHOD OF INHIBITING SPROUTING IN PLANT TISSUES

RELATED APPLICATION

The present application claims priority under 35 U.S.C. § 119(e) to U.S. Provisional Patent Application No. 62/038,621, filed Aug. 18, 2014, the content of which is herein incorporated by reference in its entirety.

TECHNOLOGY FIELD

The present invention relates to a method for inhibiting sprouting in plant seeds. More particularly, the invention relates to a method for inhibiting sprouting seeds, especially pre-harvest sprouting, by introducing a polynucleotide encoding a FCA protein into the plant.

BACKGROUND OF THE INVENTION

ABA mediates internal signaling pathways not only to adapt to abiotic stress, but also to regulate plant development. It has been shown that some ABA-insensitive mutants also display early flowering phenotype, suggesting the role of ABA in regulation of flowering (Takai et al., 2001).

FCA has been identified as a nuclear RNA-binding protein that facilitates flowering by suppressing FLC, a negative regulator of flowering (He et al., 2003; Henderson and Dean, 2004). Arabidopsis FCA contains a tryptophan-tryptophan (WW) domain and two RNA recognition motifs (RRM). FCA requires interaction with and another regulator, FY, via its WW domain for flowering time regulation (Simpson et al., 2003). The FCA RRMs are proposed to regulate chromatin silencing of single and low-copy genes (Baurle et al., 2007).

In Arabidopsis, FCA is involved in ABA-mediated regulation of flowering time and lateral root growth. FCA was once considered as an ABA receptor (Razem et al., 2006, 2008). Although the ABA binding activity is seriously questioned, FCA does regulate some ABA-mediated responses. However, the mechanism of how FCA works as an ABA regulator is unclear.

Recently, PYR/PYL/RCAR family proteins have been identified as ABA receptors (Ma et al., 2009). In Arabidopsis, the ABA sensing of these proteins is through their direct interaction with some PP2Cs, including ABI1. Such interaction inhibits the phosphatase activity of these PP2Cs and causes the activation of subclass III SnRK2s (Nishimura et al., 2009). Some transcription factors regulate ABA signaling and can be activated by SnRK2s. ABI5, a basic domain/Leu zipper (b-ZIP) transcription factor (TF), recognizes and binds the ABRE (also called ACGT-box) of many ABA-inducible promoter regions, resulting in gene activation (Casaretto and Ho, 2003). The Arabidopsis abi5 mutants have trouble in ABA response, like decreased sensitivity to ABA during seed germination and altered expression of many ABA-regulated genes, including LEA genes (Gampala et al., 2002).

This ABI5 transactivation process is dependent on the presence of another TF, viviparous1 (VP1). Co-expression of ABI5 and VP1 can mimic the ABA induction of ABRC-containing promoter, but do not affect to the ABA suppression of gene expression (Casaretto and Ho, 2003). VP1, a B3 transcription factor family member, is abundantly expressed in seeds. VP1 contains 4 conserved domains, named A1, B1, B2 and B3 which take on different functions (Suzuki et al., 1997). The N-terminus A1 domain is the functional domain of VP1 (McCarty et al., 1991). The B1 domain is responsible for the protein-protein interaction with ABI5 (Nakamura et al., 2001). B2 regulates the nuclear localization and B3 exhibits DNA binding activity (Suzuki et al., 1997; Marella and Quatrano, 2007). In addition to regulating seed development, maturation and germination, VP1 also mediates flowering and meristem activity.

Preharvest sprouting (PHS) is the premature germination of seeds while they are still on the spike before harvest. Such germination happens under prolonged rainfall and high humidity contributes, such as the weather in South Asia, North Europe and North West America. PHS reduces the quality of seeds and causes high economic loss every year. However, technologies to prevent cereal PHS are very limited.

SUMMARY OF THE INVENTION

In this study, it is unexpectedly found that the overexpression of a regulator, FCA, in rice can significantly decrease PHS hence reducing the economic loss due to PHS.

Therefore, in one aspect, the present invention provides a method for inhibition of sprouting in plant seeds, comprising:
 (i) introducing a recombinant polynucleotide encoding a FCA protein into a plant cell to obtain a transformed plant cell;
 (ii) producing a transformed plant from said transformed plant; and
 (iii) selecting a transformed plant that produces plant seeds having a reduced level of sprouting as compared to a non-transgenic plant which is not introduced with the recombinant polynucleotide encoding the FCA protein.

In another aspect, the present invention provides a transgenic plant transformed with a recombinant polynucleotide encoding a FCA protein.

In a further aspect, the present invention provides plant tissues from the transgenic plant as described herein.

In some particular embodiments, the FCA protein comprises:
 (a) an amino acid sequence having from N-terminal to C-terminal a first RNA recognition motif (RRM1), a second RNA recognition motif (RRM2) and a tryptophan-tryptophan (WW) domain, wherein
  (i) the RRM1 comprises SEQ ID NO: 4;
  (ii) the RRM2 comprises SEQ ID NO: 5; and
  (iii) the WW domain comprises SEQ ID NO: 6.

In certain embodiments, the FCA protein comprises a total of 650 to 850 (e.g. 700-800) amino acid residues in length.

In certain embodiments, the FCA protein comprises an amino acid sequence having a sequence identity of at least 80% (e.g. at least 85%, 90%, 95% or 95%) with the amino acid sequence of SEQ ID NO: 1, 2 or 3.

In certain embodiments, the RRM1 is selected from the group consisting of SEQ ID NO: 7, 10 and 13; the RRM2 is selected from the group consisting of SEQ ID NO: 8, 11 and 14; or the WW domain is selected from the group consisting of SEQ ID NO: 9, 12 and 15.

In some embodiments, the FCA protein comprises or consisting of an amino acid sequence selected from the group consisting of SEQ ID NO: 1, 2 and 3.

In some examples, the transgenic plant is monocotyledon, particularly selected from the group consisting of rice, barley, wheat, rye, oat, corn, bamboo, sugar cane, onion, leek and ginger. Specifically, the transgenic plant is rice, barley or wheat.

In some embodiments, the plant tissues are propagating materials, particularly seeds.

In some embodiments, the method of the invention is effective in inhibiting sprouting in plant seeds, occurring prior to harvest or post-harvest from the transgenic plant.

In some embodiments, the transgenic plant of the invention produces seeds having slower germination rate or generating smaller seedlings or shorter shoots after germination as compared with a non-transgenic plant which is not introduced with the recombinant polynucleotide encoding the FCA protein.

The details of one or more embodiments of the invention are set forth in the description below. Other features or advantages of the present invention will be apparent from the following detailed description of several embodiments, and also from the appending claims.

BRIEF DESCRIPTION OF THE DRAWINGS

The foregoing summary, as well as the following detailed description of the invention, will be better understood when read in conjunction with the appended drawings. For the purpose of illustrating the invention, there are shown in the drawings embodiments which are presently preferred. It should be understood, however, that the invention is not limited to the precise arrangements and instrumentalities shown.

In the drawings:

FIG. 8. Multiple sequence alignment of FCA proteins from rice (SEQ ID NO: 1), barley (SEQ ID NO: 2) and wheat (SEQ ID NO: 3). The sequence alignment was performed by ClustalW; the figure was generated by BioEdit.

DETAILED DESCRIPTION OF THE INVENTION

Figure 1:
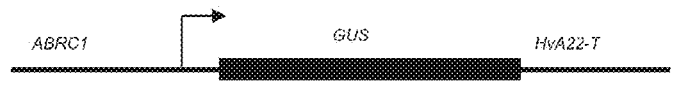
FIG. 1. FCA-overexpression enhances and FCA-RNAi suppresses ABA induced gene expression in rice aleurone cells. The reporter construct (A) ABRC1-GUS was bombarded into (B) FCA-overexpression and (C) FCA-RNAi transgenic rice embryoless half-seeds. Bars indicate GUS activities ±SE after 24 h of incubation of bombarded seeds in shooting buffer with or without 20 μM ABA.
Figure 1:
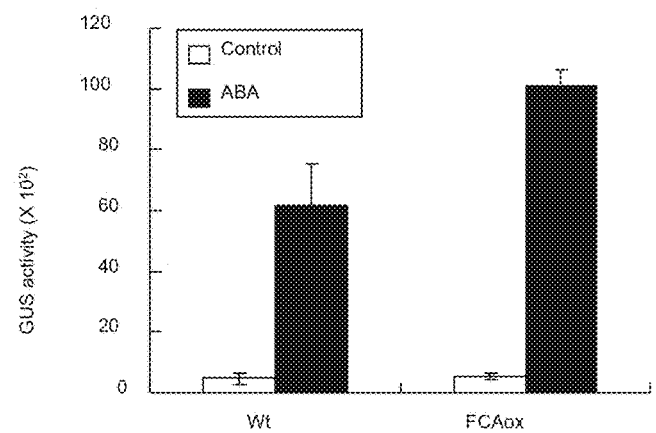
Figure 1:
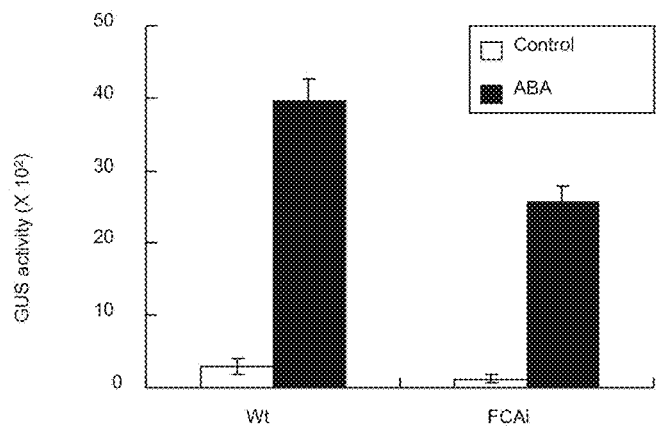

Unless defined otherwise, all technical and scientific terms used herein have the same meaning as commonly understood by a person skilled in the art to which this invention belongs.

As used herein, the singular forms "a", "an", and "the" include plural referents unless the context clearly dictates otherwise. Thus, for example, reference to "a component" includes a plurality of such components and equivalents thereof known to those skilled in the art.

The term "polynucleotide" or "nucleic acid" refers to a polymer composed of nucleotide units. Polynucleotides include naturally occurring nucleic acids, such as deoxyribonucleic acid ("DNA") and ribonucleic acid ("RNA") as well as nucleic acid analogs including those which have non-naturally occurring nucleotides. Polynucleotides can be synthesized, for example, using an automated DNA synthesizer. The term "nucleic acid" typically refers to large polynucleotides. It will be understood that when a nucleotide sequence is represented by a DNA sequence (i.e., A, T, G, C), this also includes an RNA sequence (i.e., A, U, G, C)

in which "U" replaces "T." The term "cDNA" refers to a DNA that is complementary or identical to an mRNA, in either single stranded or double stranded form.

The term "complementary" refers to the topological compatibility or matching together of interacting surfaces of two polynucleotides. Thus, the two molecules can be described as complementary, and furthermore the contact surface characteristics are complementary to each other. A first polynucleotide is complementary to a second polynucleotide if the nucleotide sequence of the first polynucleotide is identical to the nucleotide sequence of the polynucleotide binding partner of the second polynucleotide. Thus, the polynucleotide whose sequence 5'-TATAC-3' is complementary to a polynucleotide whose sequence is 5'-GTATA-3'."

The term "encoding" refers to the inherent property of specific sequences of nucleotides in a polynucleotide (e.g., a gene, a cDNA, or an mRNA) to serve as templates for synthesis of other polymers and macromolecules in biological processes having either a defined sequence of nucleotides (i.e., rRNA, tRNA and mRNA) or a defined sequence of amino acids and the biological properties resulting therefrom. Therefore, a gene encodes a protein if transcription and translation of mRNA produced by that gene produces the protein in a cell or other biological system. It is understood by a skilled person that numerous different polynucleotides and nucleic acids can encode the same polypeptide as a result of the degeneracy of the genetic code. It is also understood that skilled persons may, using routine techniques, make nucleotide substitutions that do not affect the polypeptide sequence encoded by the polynucleotides described there to reflect the codon usage of any particular host organism in which the polypeptides are to be expressed. Therefore, unless otherwise specified, a "nucleotide sequence encoding an amino acid sequence" includes all nucleotide sequences that are degenerate versions of each other and that encode the same amino acid sequence. Nucleotide sequences that encode proteins and RNA may include introns.

The term "recombinant polynucleotide" refers to a polynucleotide or nucleic acid having sequences that are not naturally joined together. A recombinantpolynucleotide may be present in the form of a vector. "Vectors" may contain a given nucleotide sequence of interest and a regulatory sequence. Vectors may be used for expressing the given nucleotide sequence (expression vector) or maintaining the given nucleotide sequence for replicating it, manipulating it or transferring it between different locations (e.g., between different organisms). Vectors can be introduced into a suitable host cell for the above mentioned purposes. A "recombinant cell" refers to a cell where a recombinant nucleic acid is introduced.

As used herein, the term "operably linked" may mean that a polynucleotide is linked to an expression control sequence in such a manner to enable expression of the polynucleotide when a proper molecule (such as a transcriptional factor) is bound to the expression control sequence.

As used herein, the term "expression control sequence" or "regulatory sequence" means a DNA sequence that regulates the expression of the operably linked nucleic acid sequence in a certain host cell.

Examples of vectors include, but are not limited to, plasmids, cosmids, phages, YACs or PACs. Typically, in vectors, the given nucleotide sequence is operatively linked to the regulatory sequence such that when the vectors are introduced into a host cell, the given nucleotide sequence can be expressed in the host cell under the control of the regulatory sequence. The regulatory sequence may comprises, for example and without limitation, a promoter sequence (e.g., the cytomegalovirus (CMV) promoter, simian virus 40 (SV40) early promoter, T7 promoter, and alcohol oxidase gene (AOX1) promoter), a start codon, a replication origin, enhancers, an operator sequence, a secretion signal sequence (e.g., α-mating factor signal) and other control sequence (e.g., Shine-Dalgano sequences and termination sequences). Preferably, vectors may further contain a marker sequence (e.g., an antibiotic resistant marker sequence) for the subsequent screening procedure. For purpose of protein production, in vectors, the given nucleotide sequence of interest may be connected to another nucleotide sequence other than the above-mentioned regulatory sequence such that a fused polypeptide is produced and beneficial to the subsequent purification procedure. Said fused polypeptide includes, but is not limited to, a His-tag fused polypeptide and a GST fused polypeptide.

Where the expression vector is constructed for a plant cell, several suitable promoters known in the art may be used, including but not limited to the Figwort mosaic virus 35S promoter, the cauliflower mosaic virus (CaMV) 35S promoter, the commelina yellow mottle virus promoter, the rice cytosolic triosephosphate isomerase (TPI) promoter, the rice actin 1 (Act 1) gene promoter, the uniquitin (Ubi) promoter, the rice amylase gene promoter, the adenine phosphoribosyltransferase (APRT) promoter of Arabidopsis, the mannopine synthase and octopine synthase promoters.

To prepare a transgenic plant, it is preferably that the expression vector as used herein carries one or more selection markers for selection of the transformed plants, for example, genes conferring the resistance to antibiotics such as hygromycin, ampicillin, gentamycine, chloramphenicol, streptomycin, kanamycin, neomycin, geneticin and tetracycline, URA3 gene, genes conferring the resistance to any other toxic compound such as certain metal ions or herbicide, such as glufosinate or bialaphos.

As used herein, the term "transgenic plant" or "transgenic line" refers to a plant that contains a recombinant nucleotide sequence that encodes a gene i.e. a transgene. The transgenic plant can be grown from a recombinant cell.

A variety of procedures that can be used to engineer a stable transgenic plant are available in this art. In one embodiment of the present invention, the transgenic plant is produced by transforming a tissue of a plant, such as a protoplast or leaf-disc of the plant, with a recombinant *Agrobacterium* cell comprising a polynucleotide encoding a desired protein (e.g. a FCA protein) and generating a whole plant from the transformed plant tissue. In another embodiment, a polynucleotide encoding a desired protein can be introduced into a plant via gene gun technology, particularly if transformation with a recombinant *Agrobacterium* cell is not efficient in the plant.

The term "polypeptide" or proteins refers to a polymer composed of amino acid residues linked via peptide bonds.

As used herein, the term "overexpression" can refer to the production of a gene product in transgenic plants that exceeds levels of production in non-transgenic plants, including but not limited to constitutive or induced expression.

The present invention provides a method for inhibiting sprouting in plantseeds, especially pre-harvest sprouting, by transforming a plant with a recombinant polynucleotide encoding a FCA protein for overexpressing the FCA protein. The present invention also provides a transgenic plant thus transformed and plant tissues obtained therefrom. The transgenic plant of the invention exhibits a reduced level of sprouting in plantseeds, as compared with a non-transgenic plant which is not introduced with the recombinant polynucleotide encoding the FCA protein. The present invention is effective in inhibiting or delaying sprouting in plant seeds, especially pre-harvest spouting, and also useful in prolonging the storage period of time of plant seeds e.g. after harvest.

In particular, the method the invention for inhibition of sprouting in plant seeds comprises:
  (i) introducing a recombinant polynucleotide encoding a FCA protein into a plant cell to obtain a transformed plant cell;
  (ii) producing a transformed plant from said transformed plant cell; and
  (iii) selecting a transformed plant that produces plant seeds having a reduced level of sprouting as compared to a non-transgenic plant which is not introduced with the recombinant polynucleotide encoding the FCA protein.

As used herein, a FCA protein is known as a nuclear RNA-binding protein that facilitates flowering, which has a WW domain and one or two RRM. In certain embodiments, the FCA protein as used herein is the one originated from rice, barley or wheat, having the amino acid sequence of SEQ ID NO: 1, 2 or 3.

It is understandable a polypeptide may have a limited number of changes or modifications that may be made within a certain portion of the polypeptide irrelevant to its activity or function and still result in a molecule with an acceptable level of equivalent biological activity or function. Modifications and changes may be made in the structure of such polypeptides and still obtain a molecule having similar or desirable characteristics. For example, certain amino acids may be substituted for other amino acids in the peptide/polypeptide structure (other than the conserved region) without appreciable loss of activity. Amino acid substitutions are generally based on the relative similarity of the amino acid side-chain substituents, for example, their hydrophobicity, hydrophilicity, charge, size, and the like. For example, arginine (Arg), lysine (Lys), and histidine (His) are all positively charged residues; and alanine (Ala), glycine (Gly) and serine (Ser) are all in a similar size. Therefore, based upon these considerations, arginine (Arg), lysine (Lys) and histidine (His); and alanine (Ala), glycine (Gly) and serine (Ser) may be defined as biologically functional equivalents. One can readily design and prepare recombinant genes for microbial expression of polypeptides having equivalent amino acid residues.

To determine the percent identity of two amino acid sequences, the sequences are aligned for optimal comparison purposes (e.g., gaps can be introduced in the sequence of a first amino acid sequence for optimal alignment with a second amino acid sequence). In calculating percent identity, typically exact matches are counted. The determination of percent homology or identity between two sequences can be accomplished using a mathematical algorithm known in the art, such as BLAST and Gapped BLAST programs, the NBLAST and XBLAST programs, or the ALIGN program.

In particular embodiments, the FCA protein as described herein comprises:
  (a) an amino acid sequence having from N-terminal to C-terminal a first RNA recognition motif (RRM1), a second RNA recognition motif (RRM2) and a trypto-phan-tryptophan (WW) domain, wherein
    (i) the RRM1 comprises SEQ ID NO: 4;
    (ii) the RRM2 comprises SEQ ID NO: 5; and
    (iii) the WW domain comprises SEQ ID NO: 6

In certain embodiments, the FCA protein comprises a total of 650 to 850 (e.g. 700-800) amino acid residues in length.

In certain embodiments, the FCA protein comprises an amino acid sequence having a sequence identity of at least 80% (e.g. at least 85%, 90%, 95% or 95%) with the amino acid sequence of SEQ ID NO: 1, 2 or 3.

In some embodiments, the RRM1 domain in the FCA protein as described herein is selected from the group consisting of SEQ ID NO: 7, 10 and 13.

In some embodiments, the RRM2 domain in the FCA protein as described herein is selected from the group consisting of SEQ ID NO: 8, 11 and 14.

In some embodiments, the WW domain in the FCA protein as described herein is selected from the group consisting of SEQ ID NO: 9, 12 and 15.

In specific embodiments, the FCA protein comprises or consisting of an amino acid sequence selected from the group consisting of SEQ ID NO: 1, 2 and 3.

As used herein, the term "sprouting" is meant to include propagation by plants from plant tissues. For example, sprouting may occur in seeds, tubes or root tubes. It includes production of seedlings, forming leaves or shoots, or the initiation of such processes to cause leaf or shoot development to begin. The inhibition of sprouting in a transgenic plant, as used herein, means suppression, delaying or retardation in such developmental process, such as a lower or slower rate of sprouting or a smaller or shorter seedling, as compared with a control or wild type plant. In some embodiments, a transgenic plant of the present invention exhibits a sprouting rate in seeds which is about 90%, 80%, 70%, 60%, 50% or less of a regular sprouting rate of a wild type plant under the same conditions.

Plants to which the inventive method can be applied include monocotyledon. Examples of monocotyledon includes but not limited to rice, barley, wheat, rye, oat, corn, bamboo, sugar cane, onion, leek and ginger. In one particular embodiment of the present invention, the transgenic plant is a transgenic cereal plant, preferably a transgenic rice plant.

According to the present invention, the transgenic plants transformed with a FCA gene leading to overexpression of a FCA protein surprisingly exhibit inhibited spouting in plant seeds such that economic loss due to early spouting can be lowered.

In some embodiments, the plant tissues are propagating materials, e.g. seeds.

In some embodiments, the method of the present invention further comprises collecting the plant seeds from the transgenic plant.

In some embodiments, the inhibition of sprouting occurs prior to harvest of the plant tissues from the transgenic plant.

In some embodiments, the inhibition of sprouting occurs post-harvest of the plant tissues from the transgenic plant.

In one particular embodiment, the transgenic plant according to the present invention produces seeds that have lower or slower germination rate or generate smaller seedlings or shorter shoots after germination as compared with those of a control plant (e.g. a non-transgenic plant); such transgenic plant is then selected and optionally the seeds are further collected.

The present invention is further illustrated by the following examples, which are provided for the purpose of demonstration rather than limitation. Those of skill in the art should, in light of the present disclosure, appreciate that many changes can be made in the specific embodiments which are disclosed and still obtain a like or similar result without departing from the spirit and scope of the invention.

EXAMPLES

Our research has focused on the function of cereal FCA. In this paper we analyze the FCA functions on complicated ABA signaling pathway and regulation of seed germination and pre-harvest sprouting.

It is found that unlike the original function of AtFCA on flowering time regulation, alteration of OsFCA expression does not affect flowering time control in transgenic rice. Overexpression of OsFCA enhances, while its RNAi suppresses, ABA up-regulation of LEA protein synthesis. However, OsFCA does not affect the well-characterized GA induction of alpha-amylase synthesis and the ABA suppression of this process. The FCA-GFP fusion protein is initially localized in the cytoplasm with a punctate pattern but then gradually translocated into nucleus. This cytosol to nucleus translocation of OsFCA is further enhanced by ABA treatment. However, a major suppressor of ABA action, abi1, a dominant mutant of protein phosphase 2C, inhibits this cytosol/nucleus translocation of OsFCA. In planta two-hybrid study reveals that OsFCA interacts with VP1, but not with ABI5 directly. In vitro pull-down assay also confirms that VP1 and FCA interact with each other. Mutation of the highly conserved WW domain in OsFCA suppresses nuclear translocation, disrupts FCA-VP1 interaction, and also suppresses ABA signaling. Our results suggest that cereal FCA plays a pivotal role in ABA signaling by transmitting ABA signaling from cytosol to nucleus where this protein interacts with the transcription factor complex of VP1/ABI5 that are required for ABA up-regulation of gene expression. Rice FCA also functions in pre-harvest sprouting regulation and may be applied in pre-harvest sprouting control in other cereal crops.

1. Material and Methods 1.1 Plant Materials

Rice (*Oryza sativa*) cultivar Tainung 67 was used in this study. Rice seedlings were grown in Kimura B nutrient solution at 28° C., 16L/8D photoperiod. Barley seeds (*Hordeum vulgare* L. cv. Himalaya) were used in all the transient assays. Embryoless half-seeds were prepared as described (Gomez-Cadenas et al., 2001).

1.2 Plasmid Construction

Rice FCA cDNA clones (GenBank Accession Numbers AK073225 and AK058419) were supplied by Rice Genome Resource Center (RGRC) of National Institute of Agricultural Sciences (NIAS). Coding region of rice FCA was amplified from FCA cDNA clone by PCR. Coding region of barley FCA was amplified from total RNA of barley seed by RT-PCR. For underexpression of FCA, nucleotide number 307-822 of rice FCA ORF and nucleotide number 1532-1945 of barley FCA ORF were amplified. All PCR products were T/A cloned into pCR8/GW/TOPO vector (Invitrogen). Sequences and orientations of inserts in vector were confirmed by sequencing. In this study, Gateway®-compatible (Invitrogen, Karlsruhe, Germany) vectors were used to generate plasmid constructs for all transient experiments and plant transformation. Insert DNA fragments in pCR8/GW/TOPO vectors were further subcloned into destination vectors by LR recombination using LR clonase (Invitrogen) according to manufacturer's instruction. Destination vectors are pANDA (Miki and Shimamoto, 2004) and pBI-Ubi-GW for plant transformation, pANDA-mini (Miki and Shimamoto, 2004) and pUC-Ubi-GW for transient expression assay. For transient assays, the reporter constructs ABRC3-GUS and Amy32b-GUS and the effector constructs 35S-ZmVP1 and Ubi-HvABI5 have been described (McCarty et al., 1991; Lanahan et al., 1992; Armstrong et al., 1995; Casaretto and Ho, 2003). A constitutive construct, pAHC18 (Ubi1-LUC) (Shen et al., 1993) was uses as the internal control.

1.3 Plant Transformation

Plasmid pBI-Ubi-OsFCA and pBI-Ubi-OsFCA-RNAi were introduced into *Agrobacterium tumefaciens* strain LBA4404, and rice transformation was performed as described (Chen et al., 2002).

1.4 Germination Test

Rice seeds were dehulled and sterilized by 25% commercial bleach plus 0.1% tween-20 for 30 min and followed by 6 times washes with sterilized water. Sterilized seeds were put on 9 -cm petri-dish containing 8-10 ml of water with or without ABA. Petri-dishes were incubated at 28° C. in dark. Seeds with 2-3 mm hypocotyl were scored daily as seed germination for up to 7 days for overexpression lines and 10 days for RNAi lines. In each experiment, 30 seeds per petr-dish and three petri-dishes per line were used. Seed germination was repeated three times.

1.5 Evaluation of Pre-harvest Sprouting (PHS)

Pre-harvest sprouting (PHS) of transgenic rice was evaluated as described (Groos et al., 2002). Intact spikes of wild type and transgenic rice were excised at 40 to 42 days after heading, surface sterilized by 25% commercial bleach for 30 minutes and washed by plenty of sterilized water 6 times and then immersed in deionized water for 4 hours in test tube. Extra water was removed and kept about 1 cm water in the bottom of tube to keep moisture. The number of sprouted and non-sprouted grains was recorded for each spike after incubation for 7 to 11 days at 28 C.

Figure 2:
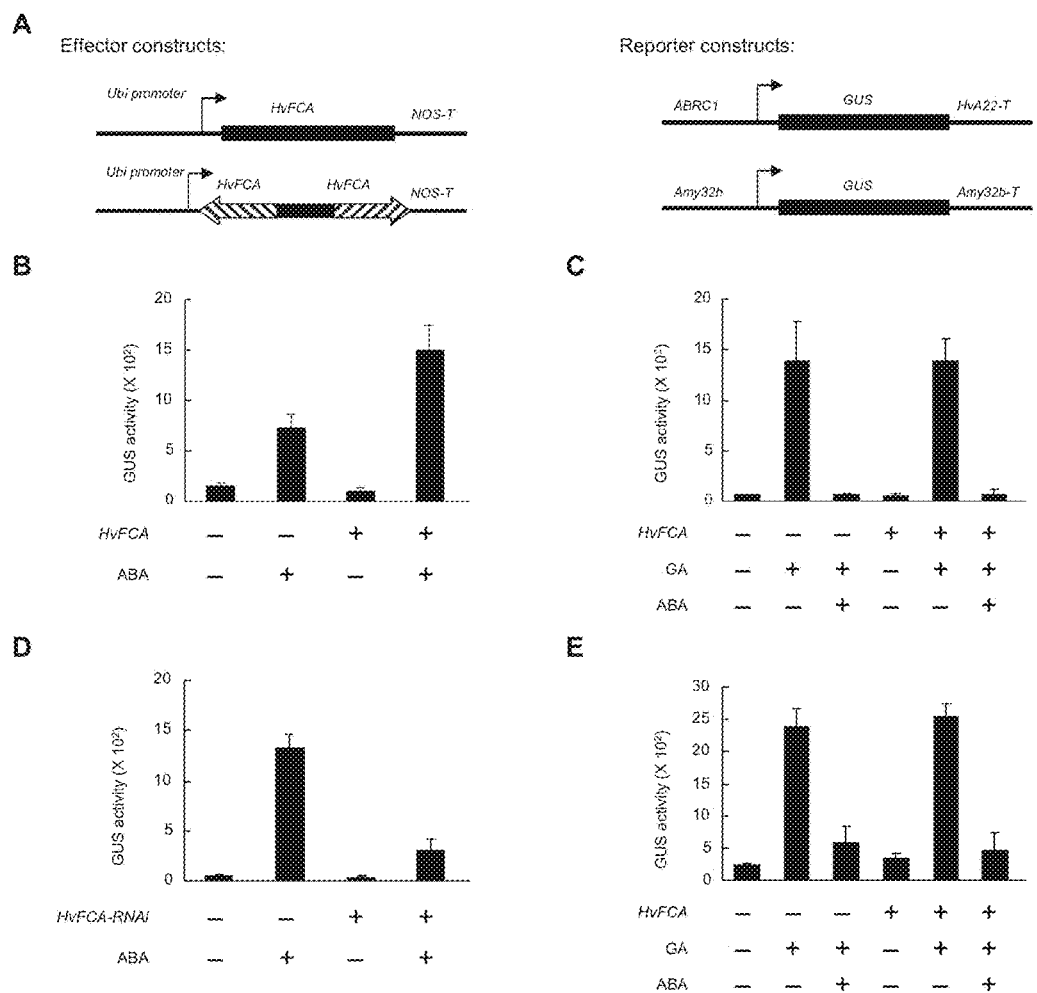
FIG. 2. FCA alters ABA but not GA pathway in barley aleurone cells. (A) Schemes of the reporter and effector constructs used in transient expression assays. (B) FCA-overexpression enhances and (D) FCA-RNAi suppresses ABA induced gene expression in barley aleurone cells. (C and E) GA induced gene expression is not affected. The reporter construct ABRC1-GUS or Amy32b-GUS was cobombarded into barley embryoless half-seeds with (+) or without (−) effector constructs Ubi-HvFCA-RNAi or Ubi-HvFCA. Bars indicate GUS activities ±SE after 24 h of incubation of bombarded embryoless half-seeds in shooting buffer with or without 20 μM ABA or 1 μM GA.

2. Results 2.1 FCA-overexpression Enhances and FCA-RNAi Suppresses ABA Induced Gene Expression in Transgenic Rice Aleurone Cells and Barley Aleurone Cells To test whether FCA is important for induction of ABA-response genes, we use seeds from both FCA overexpression lines and FCA-RNAi lines as materials for expression assay. In wild type, the ABRC1-GUS reporter is highly induced in rice aleurone cells by ABA treatment. The ABA induction level of ABA-responsive reporter gene expression in FCA over expression transgenic lines is about 30% higher than that in wild type (FIG. 1, panel A). In contrast, the induction level is suppressed in FCA-RNAi transgenic lines (FIG. 1, panel B). These transgenic plants studies show that FCA is important in ABA signaling. For further study of function of FCA, transient expression assay in barley aleurone cells was performed. Effector Ubi-FCA or Ubi-FCA-RNAi was co-bombarded into barley aleurone cells with the reporter constructs. Similar to in rice aleurone cells, ABRC1-GUS reporter is highly induced in barley aleurone cells by ABA treatment. Overexpression of FCA enhances the ABA responsive induction about 25% (FIG. 2, panel B), and RNAi suppression of FCA decreases the induction (FIG. 2, panel D). However, the other two signaling pathways, i.e. GA induction and ABA suppression of a-amylase gene expressions, are not affected at all by either over expression or RNAi of FCA (FIG. 2, panels C and E). These indicate FCA only works as an enhancer in ABA signaling.

Figure 3:
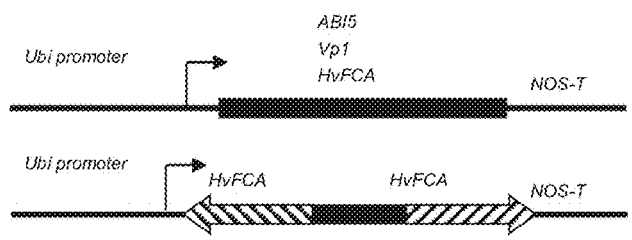
FIG. 3. FCA-RNAi suppresses and FCA-overexpression enhances VP1/ABI5 induced gene expression in barley aleurone cells. (A) Schemes of the reporter and effector constructs used in transient expression assays. The reporter construct ABRC1-GUS was cobombarded into barley embryoless half-seeds with (+) or without (−) effector constructs Ubi-VP1, Ubi-ABI5, and (B) Ubi-HvFCA or (C) Ubi-HvFCA-RNAi. Bars indicate GUS activities ±SE after 24 h of incubation of bombarded embryoless half-seeds in shooting buffer.
Figure 3:
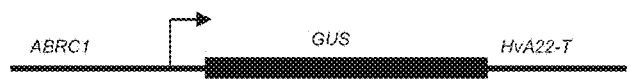
Figure 3:
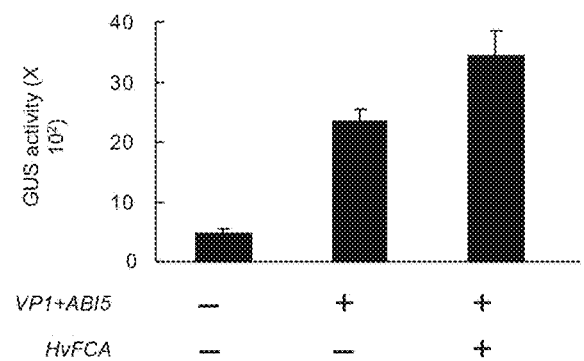
Figure 3:
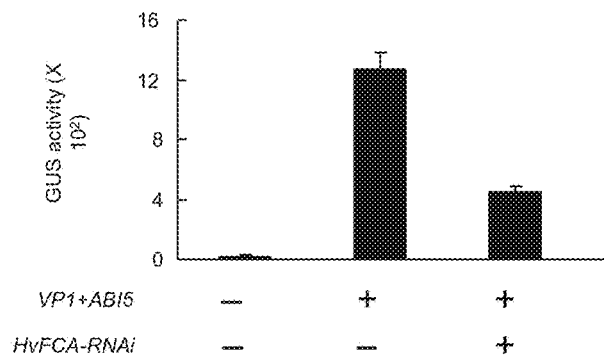

2.2 FCA-overexpression Enhances and FCA-RNAi Suppresses VP1/ABI5 induced gene expression in barley aleurone cells In plant seeds, the bZIP transcriptional factor ABI5 and VP1 play critical role for ABA responsive gene expression. Co-expression of ABI5 and VP1 in barley aleurone cells are sufficient to induce ABA-responsive LEA gene expression. To study whether FCA also enhance the ABI5/VP1 induction ability, we co-expressed these genes in barley aleurone cells and see their effect. Co-expression of ABI5 and VP1 induce the ABA-response reporter genes expression without ABA treatment (FIG. 3). Over expression of FCA enhance the ABI5/VP1 induction ability about 30% (FIG. 3, panel B), and RNAi suppression of FCA decreases this induction (FIG. 3, panel C). This indicates FCA may function directly to ABI5/VP1 in gene transcription processes.

Figure 4:
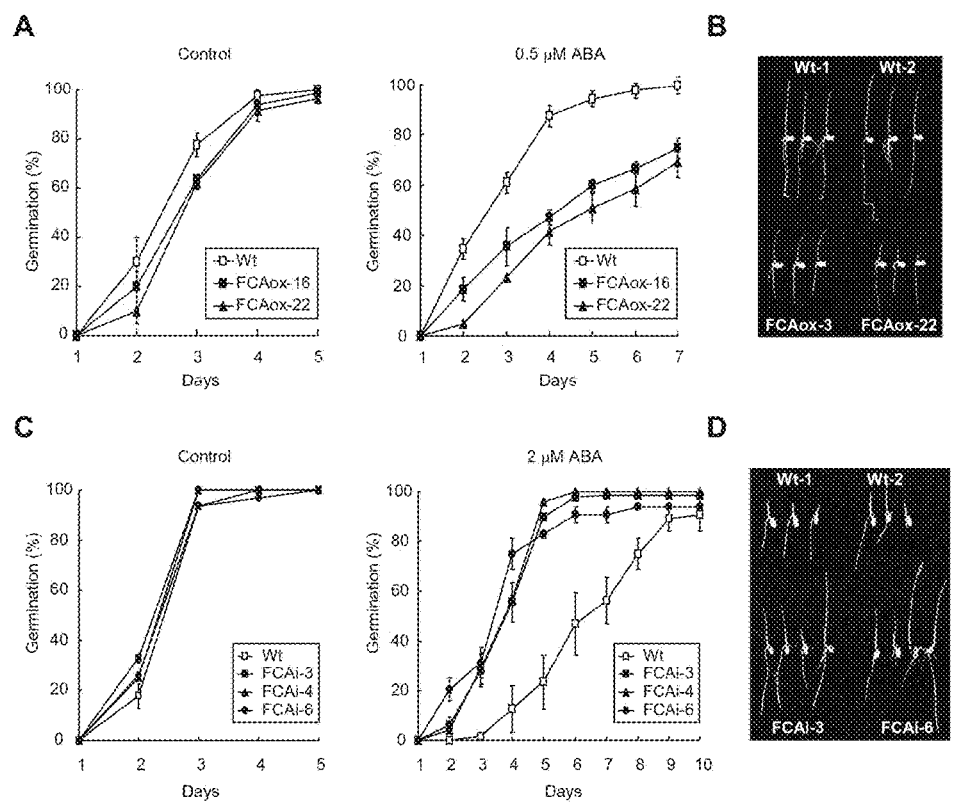
FIG. 4. Overexpression of FCA leads to ABA hypersensitivity and FCA-RNAi leads to ABA hyposensitivity in seed germination. Seed germination time courses of (A) FCA-overexpression and (C) FCA-RNAi transgenic rice. Sterilized rice seeds were incubated in 9-cm petri-dish containing 8-10 ml of water with or without ABA at 28° C. in dark. Data shown are means ±SE of three replicates. At least 30 seeds per transgenic lines were measured in each replicate. Photographs of (B) FCA-overexpression and (D) FCA-RNAi seedlings growing on ABA containing vertical agar medium were taken at the end of experiment.

2.3 Overexpression of FCA Leads to ABA Hypersensitivity and FCA-RNAi Leads to ABA Hyposensitivity in Rice Seed Germination To elucidate the biological function of OsFCA in rice, transgenic rice harboring OsFCA-overexpression and FCA-RNAi constructs were generated. Homozygous seeds were subjected to seed germination test. In water, OsFCA-overexpression and FCA-RNAi transgenic rice germinated as well as wild type did (FIG. 4, panels A and C). But in 1 µM ABA, germination rate of FCA-overexpression transgenic rice was slower than that of wild type (FIG. 4, panel A). This retardation indicated that FCA-overexpression lead to ABA hypersensitivity in seed germination. In contrast, faster germination rate of FCA-RNAi transgenic rice in 2 µM ABA (FIG. 4, panel C) indicated that FCA-RNAi leads to ABA hyposensitivity in seed germination. Seedlings of FCA-overexpression transgenic rice were smaller and FCA-RNAi transgenic rice were larger than that of wild type after growing on ABA containing medium (FIG. 4, panels B and D).

2.4 Overexpression of FCA Prevents Pre-harvest Sprouting in Rice

Figure 5:
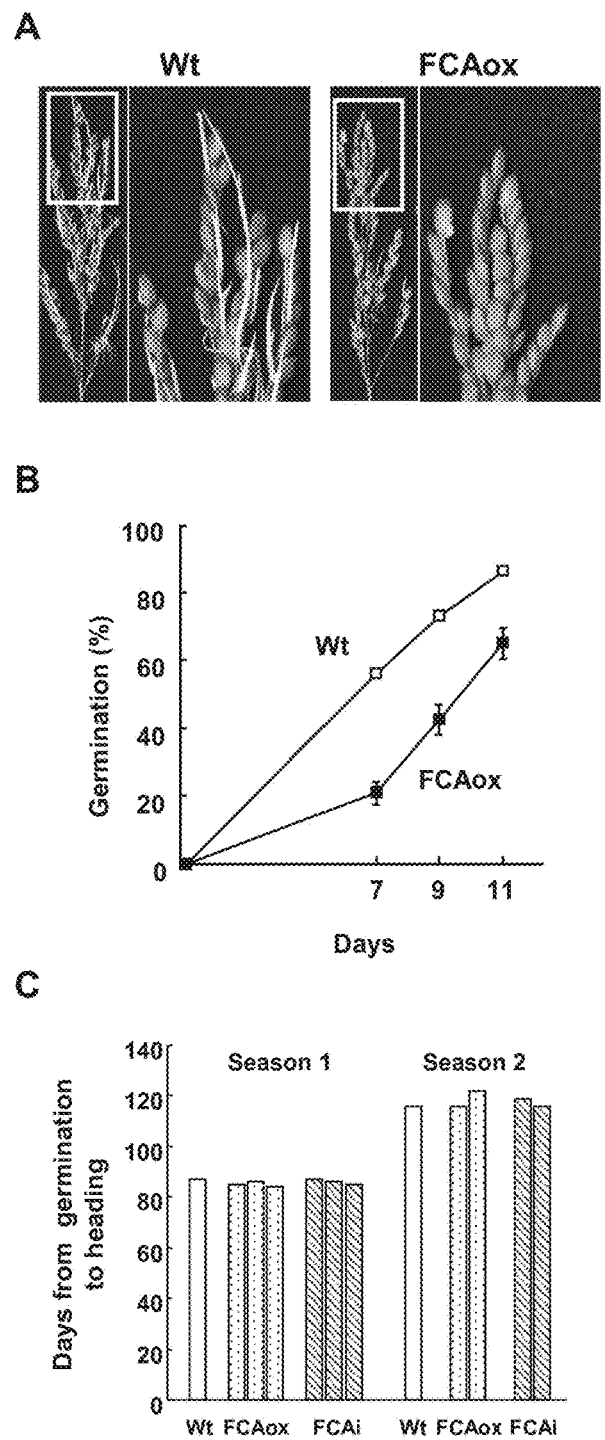
FIG. 5. Overexpression of FCA suppresses pre-harvest sprouting but not alters heading date. (A) Spikes excised 40 to 42 days after heading were incubated in moisture chamber at 25 C. Photographs were taken at day 11. (B) The numbers of spouting grains on moisturized spikes were scored at day 7, 9 and 11. (C) Heading dates were recorded from germination to appearance of the first panicle of about 1 cm in length. Results from two growing seasons were presented.
Figure 6:
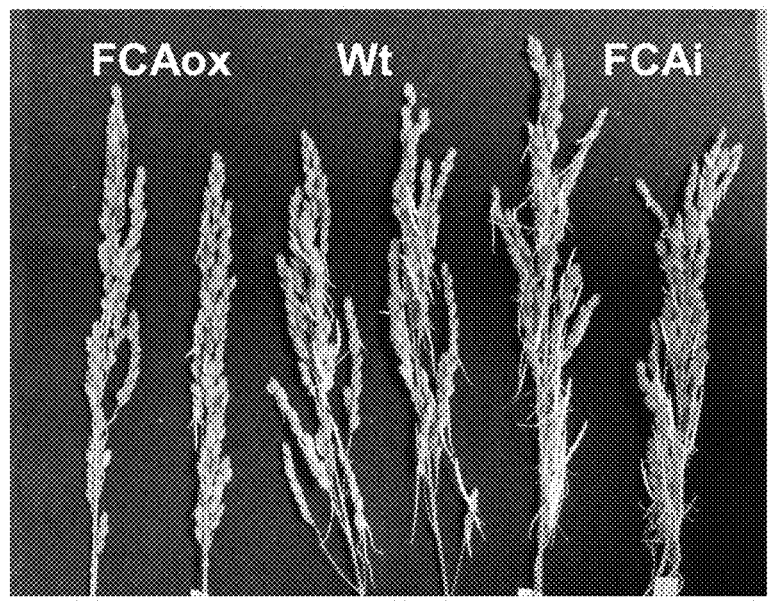
FIG. 6. Overexpression of FCA suppresses pre-harvest sprouting. (A) Spikes excised 37 to 38 days after heading were incubated in moisture chamber at 25 C. Photographs were taken at day 11. (B) The numbers of spouting grains on moisturized spikes were scored at day 11.
Figure 6:
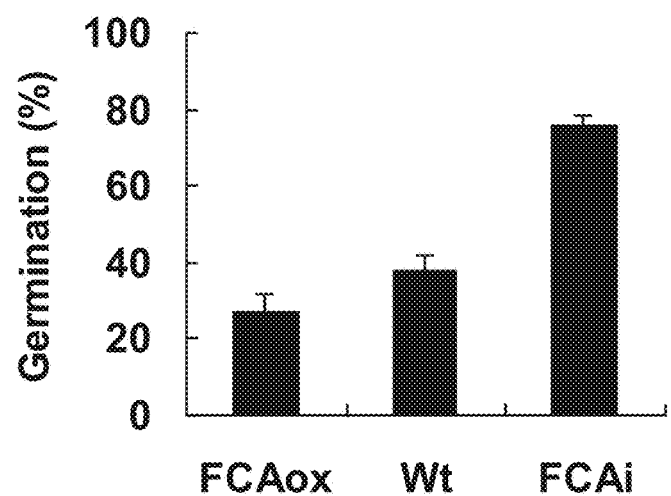
Figure 7:
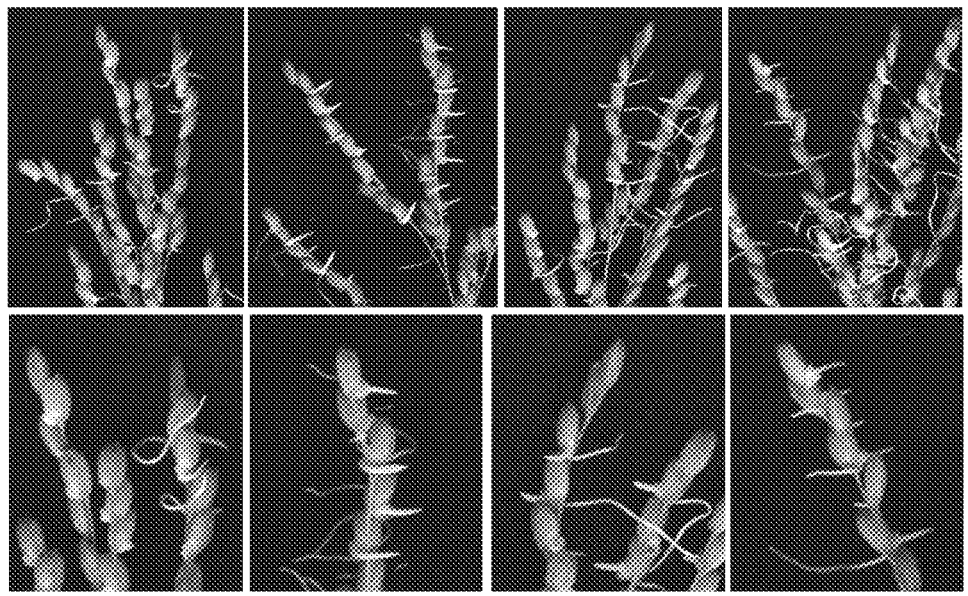
FIG. 7. Overexpression of FCA suppresses pre-harvest sprouting. Excised mature spikes were incubated in moisture chamber at 25 C. Photographs were taken at day 3.
Figure 7:
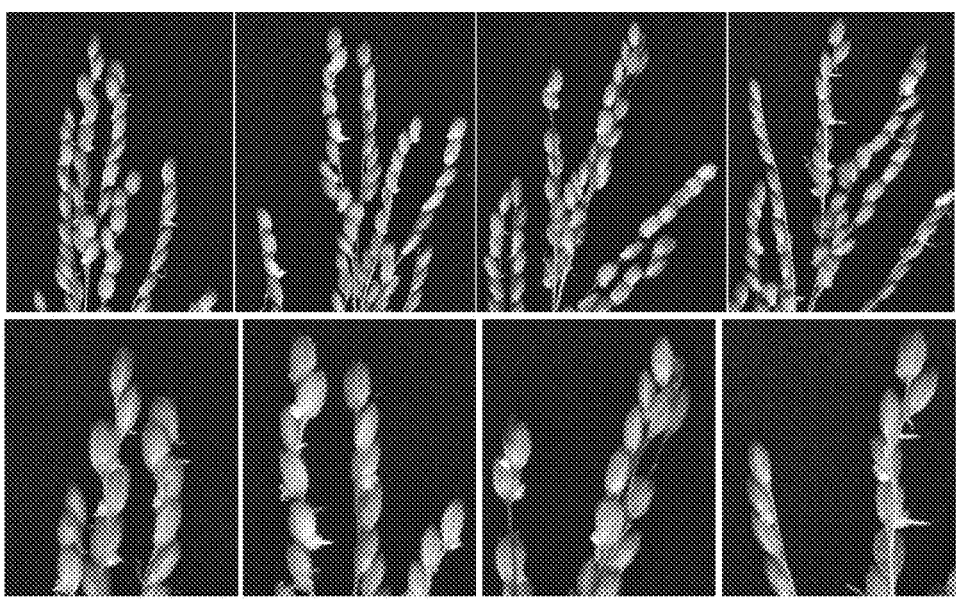

Based on the flowering time regulatory function of Arabidopsis FCA, flowering time of transgenic rice was investigated. In two growing season investigation, FCA-overexpression and FCA-RNAi seemed not to alter the heading dates (FIG. 5, panel C). But the spikes of FCA-overexpression transgenic rice showed tolerance to pre-harvest sprouting (PHS) (FIG. 5, panels A and B). Compared with wild type, less FCA-overexpression grains in spikes sprouted under high moisture condition (FIG. 5, panel B). Sprouting shoots in wild type spike were longer than those in FCA-overexpression spike (FIG. 5, panel A). More data in FIGS. 6 and 7 show the prevention of PHS in FCA-overexpression transgenic rice.

Figure 8:
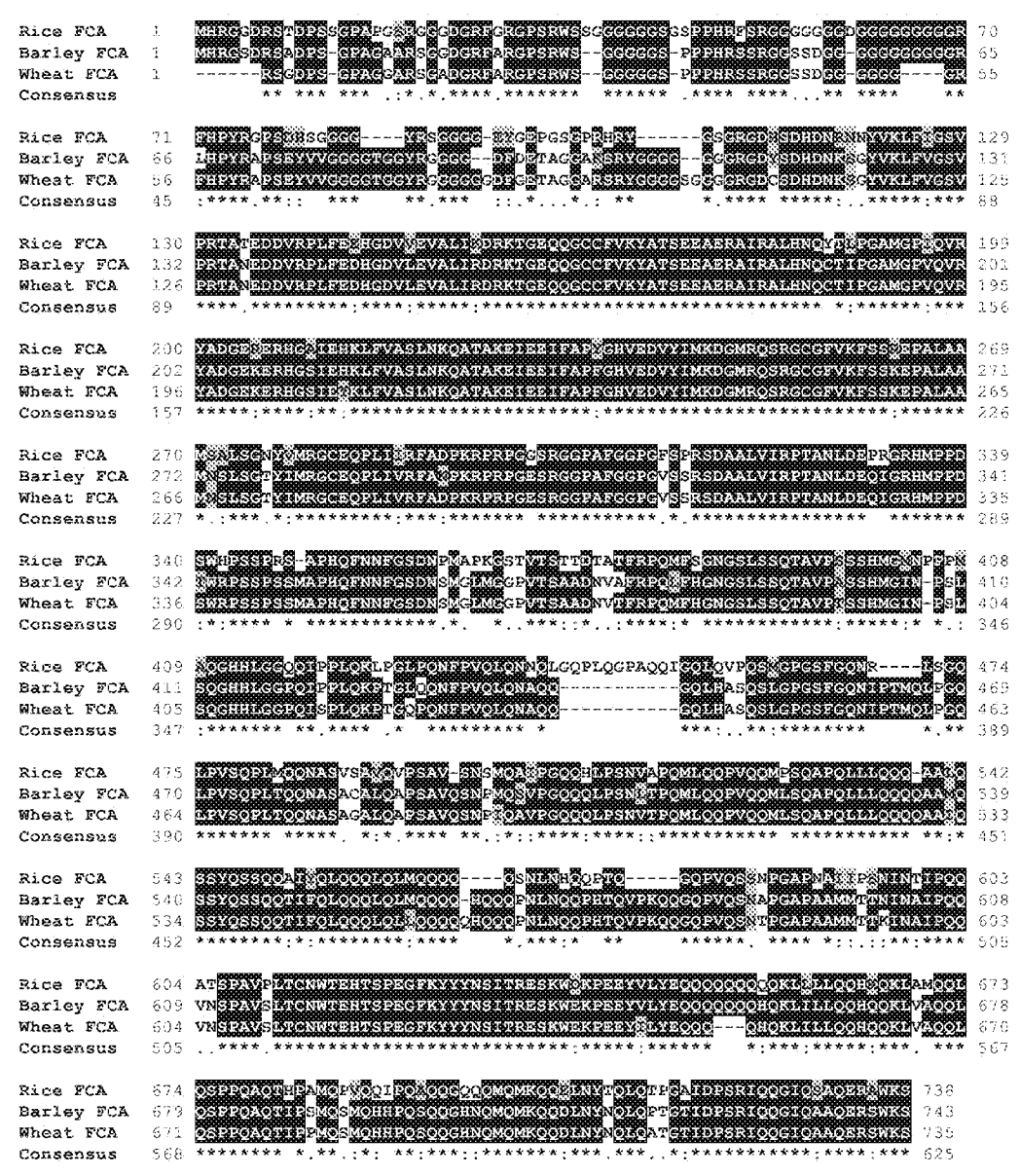
Figure 9:
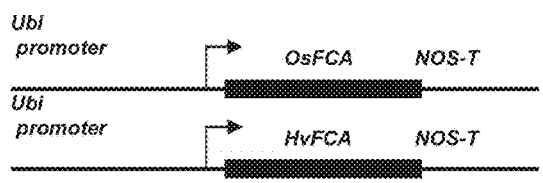
FIG. 9. FCA-overexpression enhances ABA induced gene expression in barley aleurone cells. (A) Schemes of the reporter and effector constructs used in transient expression assays. (B) The reporter construct ABRC1-GUS was cobombarded into barley embryoless half-seeds with (+) or without (−) effector constructs Ubi-HvFCA or Ubi-OsFCA. Bars indicate GUS activities ±SE after 24 h of incubation of bombarded embryoless half-seeds in shooting buffer with (+) or without (−) 10 μM ABA.
Figure 9:
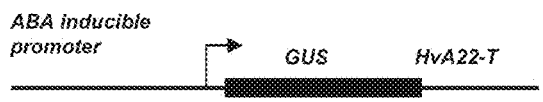
Figure 9:
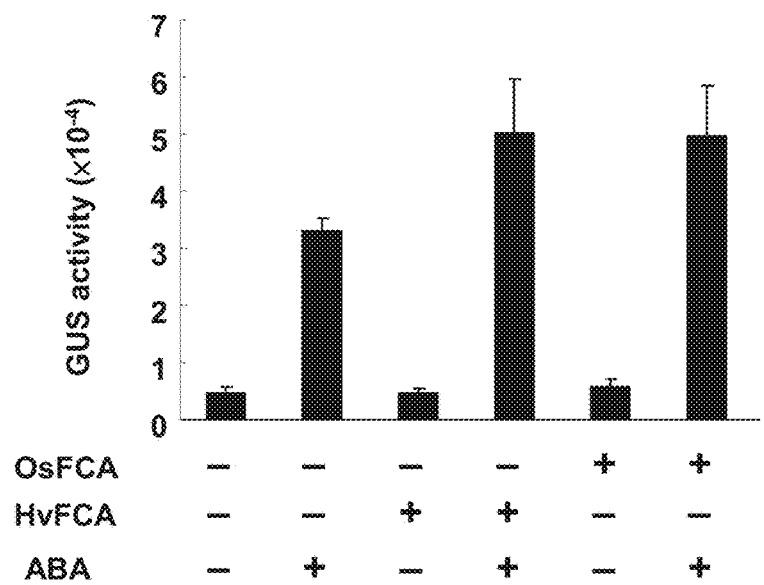
Figure 10:
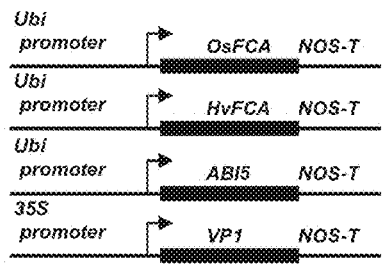
FIG. 10. FCA-overexpression enhances VP1/ABI5 induced gene expression in barley aleurone cells. (A) Schemes of the reporter and effector constructs used in transient expression assays. The reporter construct ABRC1-GUS was cobombarded into barley embryoless half-seeds with (+) or without (−) effector constructs 35S-VP1, Ubi-ABI5, and (B) Ubi-OsFCA or (C) Ubi-HvFCA. Bars indicate GUS activities ±SE after 24 h of incubation of bombarded embryoless half-seeds in shooting buffer.
Figure 10:
Figure 10:
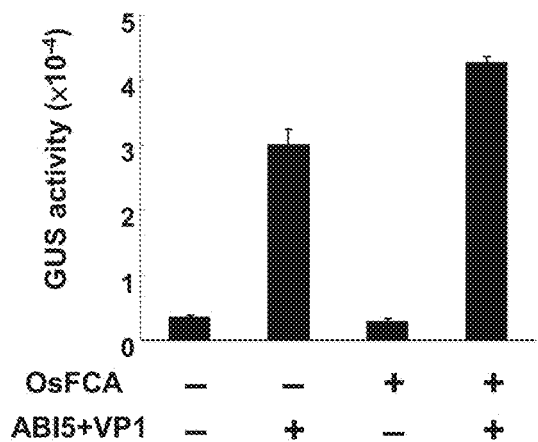
Figure 10:
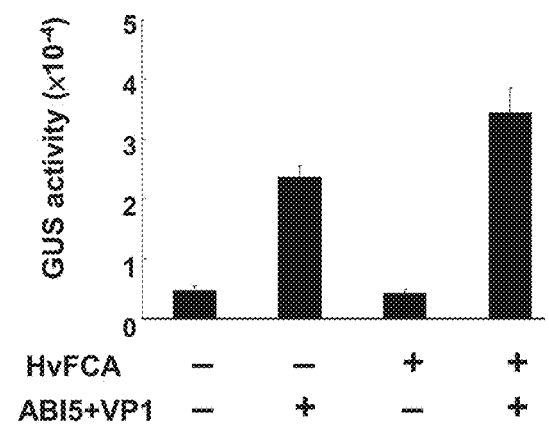

2.5 Application of Rice FCA in Solving Worldwide Pre-harvest Spouting (PHS) Problem in Rice, Barley and Wheat Production Pre-harvest sprouting (PHS) of cereals is a worldwide problem that can affect a wide range of cereals including barley, maize, rice, rye and sorghum. Grain germination occurs when still in the spike during wet conditions close to harvest time. This sprouting damage lowers the value of crops and results in great agricultural economic losses (Gubler et al., 2005; Fang and Chu, 2008). For solving this problem, rice FCA which functions in PHS prevention may be applied in barley and wheat PHS control. Amino acid sequences alignment (FIG. 8) shows high similarity between barley, wheat and rice FCA. Barley FCA also shows a similar function in enhancement of ABA induction (FIG. 9) and VP1/ABI5 induced gene expression (FIG. 10). These results suggest that cereal FCA may play a similar role in regulation of seed germination and PHS and imply the possibility to use rice FCA in PHS control in other cereal crops.

SEQUENCE INFORMATION

SEQ ID NO: 1 Rice FCA
(RRM1, RRM2 and WW domain are indicated with bold letters (SEQ ID NO: 7), bold letters plus a dashed line (SEQ ID NO: 8) and bold letters plus a dotted line (SEQ ID NO: 9), from N to C terminals, respectively)
MHRGGDRSTDPSSGPAPGSRGGGDGRFGRGPSRWSSGGGGGGSGSPPHRF

SRGGGGGGDGGGGGGGGGRFHPYRGPSDHSGGGYRSGGGGEYGEPGSG

PRHRYGSGRGDHSDHDNRNNYVKLFIGSVPRTATEDDVRPLFEEHGDVVE

VALIKDRKTGEQQGCCFVKYATSEEAERAIRALHNQYTLPGAMGPIQVRY

ADGERERHGAIEHKLFVASLNKQATAKEIEEIFAPYGHVEDVYIMKDGMR

QSRGCGFVKFSSREPALAAMSALSGNYVMRGCEQPLIIRFADPKRPRPGG

SRGGPAFGGPGFSPRSDAALVIRPTANLDEPRGRHMPPDSWHPSSPRSAP

HQFNNFGSDNPMAPKGSTVTSTTDTATFRPQMFSGNGSLSSQTAVPSSSH

MGMNPPPMAQGHHLGGQQIPPLQKLPGLPQNFPVQLQNNQLGQPLQGPAQ

QIGQLQVPQSMGPGSFGQNRLSGQLPVSQPLMQQNASVSAVQVPSAVSNS

MQAIPGQQHLPSNVAPQMLQQPVQQMPSQAPQLLLQQQAALQSSYQSSQQ

AIYQLQQQLQLMQQQQQSNLNHQQPTQGQPVQSSNPGAPNAIIPSNINTI

PQQATSPAVPLTCNWTEHTSPEGFKYYNSITRESKWDKPEEYVLYEQQQ

QQQQQQKLLLLQQHKQKLAMQQLQSPPQAQTHPAMQPVQQIPQAQQGQQQ

MQMKQQELNYTQLQTPGAIDPSRIQQGIQSAQERAWKS

SEQ ID NO: 2 Barley FCA
(RRM1, RRM2 and WW domain are indicated with bold letters (SEQ ID NO: 10), bold letters plus a dashed line (SEQ ID NO: 11) and bold letters plus a dotted line (SEQ ID NO: 12), N to C terminals, respectively)
MHRGSDRSADPSGPAGAARSGGDGRFARGPSRWSGGGGGSPPPHRSSRGG

SSDGGGGGGGGGGRLHPYRAPSEYVVGGGGTGGYRGGGGDFDETAGGAK

SRYGGGGGGRGDYSDHDNKSGYVKLFVGSVPRTANEDDVRPLFEDHGDV

LEVALIRDRKTGEQQGCCFVKYATSEEAERAIRALHNQCTIPGAMGPVQV

RYADGEKERHGSIEHKLFVASLNKQATAKEIEEIFAPFGHVEDVYIMKDG

MRQSRGCGFVKFSSKEPALAAMNSLSGTYIMRGCEQPLIVRFANPKRPRP

GESRGGPAFGGPGVSSRSDAALVIRPTANLDEQIGRHMPPDTWRPSSPSS

MAPHQFNNFGSDNSMGLMGGPVTSAADNVAFRPQLFHGNGSLSSQTAVPA

SSHMGINPSLSQGHHLGGPQIPPLQKPTGLQQNFPVQLQNAQQGQLHASQ

SLGPGSFGQNIPTMQLPGQLPVSQPLTQQNASACALQAPSAVQSNPMQSV

PGQQQLPSNLTPQMLQQPVQQMLSQAPQLLLQQQQAAMQSSYQSSQQTIF

QLQQQLQLMQQQQHQQQPNLNQQPHTQVPKQQGQPVQSNAPGAPAAMMTT

NINAIPQQVNSPAVSLTCNWTEHTSPEGFKYYNSITRESKWEKPEEYVL

YEQQQQQQQHQKLILLQQHQQKLVAQQLQSPPQAQTIPSMQSMQHHPQSQ

QGHNQMQMKQQDLNYNQLQPTGTIDPSRIQQGIQAAQERSWKS

SEQ ID NO: 3 Wheat FCA
(RRM1, RRM2 and WW domain are indicated with bold
letters (SEQ ID NO: 13), bold letters plus a
dashed line (SEQ ID NO: 14) and bold letters plus
a dotted line (SEQ ID NO: 15), N to C terminals,
respectively)
RSGDPSGPAGGARSGADGRFARGPSRWSGGGGGSPPPHRSSRGGSSDGGG

GGGGRFHPYRAPSEYVVGGGGTGGYRGGGGGGDFGETAGGARSRYGGGGS

GGGGRGDCSDHDNKSGYVKLFVGSVPRTANEDDVRPLFEDHGDVLEVALI

RDRKTGEQQGCCFVKYATSEEAERAIRALHNQCTIPGAMGPVQVRYADGE

KERHGSIEYKLFVASLNKQATAKEIEEIFAPFGHVEDVYIMKDGMRQSRG

CGFVKFSSKEPALAAMNSLSGTYIMRGCEQPLIVRFADPKRPRPGESRGG

PAFGGPGVSSRSDAALVIRPTANLDEQIGRHMPPDSWRPSSPSSMAPHQF

NNFGSDNSMGLMGGPVTSAADNVTFRPQMFHGNGSLSSQTAVPTSSHMGI

NPSLSQGHHLGGPQISPLQKPTGQPQNFPVQLQNAQQGQLHASQSLGPGS

FGQNIPTMQLPGQLPVSQPLTQQNASAGALQAPSAVQSNPIQAVPGQQQL

PSNVTPQMLQQPVQQMLSQAPQLLLQQQQAAIQSSYQSSQQTIFQLQQQL

QLLQQQQQHQQQPNLNQQPHTQVPKQQGQPVQSNTPGAPAAMMTTKINAI

PQQVNSPAVSLTCNWTEHTSPEGFKYYYNSITRESKWEKPEEYILYEQQQ

QHQKLILLQQHQQKLVAQQLQSPPQAQTIPPMQSMQHHPQSQQGHNQMQM

KQQDLNYNQLQATGTIDPSRIQQGIQAAQERSWKS

SEQ ID NO: 4, a consensus RRM1 sequence,
corresponding to position 123 to 202 of SEQ ID NO:
1
KLFXGSVPRTAXEDDVRPLFEXHGDVXEVALIXDRKTGEQQGCCFVKYAT

SEEAERAIRALHNQXTXPGAMGPXQVRYAD (X means any amino acid residues).
SEQ ID NO: 5, a consensus RRM2 sequence,
corresponding to position 214 to 292 of SEQ ID NO:
1
KLFVASLNKQATAKEIEEIFAPXGHVEDVYIMKDGMRQSRGCGFVKFSSX

EPALAAMXXLSGXYXMRGCEQPLIXRFAX (X means any amino acid residues).
SEQ ID NO: 6, a consensus WW domain sequence,
corresponding to positions 604 to 646 of SEQ ID
NO: 1
XXSPAVXLTCNWTEHTSPEGFKYYYNSITRESKWXKPEEYXLY (X means any amino acid residues).
SEQ ID NO: 7, a RRM1 sequence in Rice FCA (SEQ ID
NO: 1)
KLFIGSVPRTATEDDVRPLFEEHGDVVEVALIKDRKTGEQQGCCFVKYAT

SEEAERAIRALHNQYTLPGAMGPIQVRYAD

SEQ ID NO: 8, a RRM2 sequence in Rice FCA (SEQ ID
NO: 1)
KLFVASLNKQATAKEIEEIFAPYGHVEDVYIMKDGMRQSRGCGFVKFSSR

EPALAAMSALSGNYVMRGCEQPLIIRFAD

SEQ ID NO: 9, a WW domain sequence in Rice FCA
(SEQ ID NO: 1)
ATSPAVPLTCNWTEHTSPEGFKYYYNSITRESKWDKPEEYVLY SEQ ID NO: 10, a RRM1 sequence in Barley FCA (SEQ
ID NO: 2)
KLFVGSVPRTANEDDVRPLFEDHGDVLEVALIRDRKTGEQQGCCFVKYAT

SEEAERAIRALHNQCTIPGAMGPVQVRYAD

SEQ ID NO: 11, a RRM2 sequence in Barley FCA (SEQ
ID NO: 2)
KLFVASLNKQATAKEIEEIFAPFGHVEDVYIMKDGMRQSRGCGFVKFSSK

EPALAAMNSLSGTYIMRGCEQPLIVRFAN

SEQ ID NO: 12, a WW domain sequence in Barley FCA
(SEQ ID NO: 2)
VNSPAVSLTCNWTEHTSPEGFKYYYNSITRESKWEKPEEYVLY SEQ ID NO: 13, a RRM1 sequence in Wheat FCA (SEQ
ID NO: 3)
KLFVGSVPRTANEDDVRPLFEDHGDVLEVALIRDRKTGEQQGCCFVKYAT

SEEAERAIRALHNQCTIPGAMGPVQVRYAD

SEQ ID NO: 14, a RRM2 sequence in Wheat FCA (SEQ
ID NO: 3)
KLFVASLNKQATAKEIEEIFAPFGHVEDVYIMKDGMRQSRGCGFVKFSSK

EPALAAMNSLSGTYIMRGCEQPLIVRFAD

SEQ ID NO: 15, a WW domain sequence in Wheat FCA
(SEQ ID NO: 3)
VNSPAVSLTCNWTEHTSPEGFKYYYNSITRESKWEKPEEYILY

REFERENCES

Armstrong, F., Leung, J., Grabov, A., Brearley, J., Giraudat, J., and Blatt, M. R. (1995). Sensitivity to abscisic acid of guard-cell K+ channels is suppressed by abi1-1, a mutant Arabidopsis gene encoding a putative protein phosphatase. Proc Natl Acad Sci U S A 92, 9520-9524.

Baurle, I., Smith, L., Baulcombe, D. C., and Dean, C. (2007). Widespread role for the flowering-time regulators FCA and FPA in RNA-mediated chromatin silencing. Science (New York, N.Y. 318, 109-112.

Casaretto, J., and Ho, T. H. (2003). The transcription factors HvABI5 and HvVP1 are required for the abscisic acid induction of gene expression in barley aleurone cells. Plant Cell 15, 271-284.

Chen, P. W., Lu, C. A., Yu, T. S., Tseng, T. H., Wang, C. S., and Yu, S. M. (2002). Rice alpha-amylase transcriptional enhancers direct multiple mode regulation of promoters in transgenic rice. The Journal of biological chemistry 277, 13641-13649.

Fang, J., and Chu, C. (2008). Abscisic acid and the pre-harvest sprouting in cereals. Plant signaling & behavior 3, 1046-1048.

Gampala, S. S., Finkelstein, R. R., Sun, S. S., and Rock, C. D. (2002). ABI5 interacts with abscisic acid signaling effectors in rice protoplasts. The Journal of biological chemistry 277, 1689-1694.

Gomez-Cadenas, A., Zentella, R., Walker-Simmons, M. K., and Ho, T. H. (2001). Gibberellin/abscisic acid antagonism in barley aleurone cells: site of action of the protein kinase PKABA1 in relation to gibberellin signaling molecules. Plant Cell 13, 667-679.

Groos, C., Gay, G., Perretant, M. R., Gervais, L., Bernard, M., Dedryver, F., and Charmet, G. (2002). Study of the relationship between pre-harvest sprouting and grain color by quantitative trait loci analysis in a whitexred grain bread-wheat cross. TAG. Theoretical and applied genetics. Theoretische und angewandte Genetik 104, 39-47.

Gubler, F., Millar, A. A., and Jacobsen, J. V. (2005). Dormancy release, ABA and pre-harvest sprouting. Current opinion in plant biology 8, 183-187.

He, Y., Michaels, S. D., and Amasino, R. M. (2003). Regulation of flowering time by histone acetylation in Arabidopsis. Science (New York, N.Y. 302, 1751-1754.

Henderson, I. R., and Dean, C. (2004). Control of Arabidopsis flowering: the chill before the bloom. Development 131, 3829-3838.

Lanahan, M. B., Ho, T. H., Rogers, S. W., and Rogers, J. C. (1992). A gibberellin response complex in cereal alpha-amylase gene promoters. Plant Cell 4, 203-211.

Ma, Y., Szostkiewicz, I., Korte, A., Moes, D., Yang, Y., Christmann, A., and Grill, E. (2009). Regulators of PP2C phosphatase activity function as abscisic acid sensors. Science (New York, N.Y. 324, 1064-1068.

Marella, H. H., and Quatrano, R. S. (2007). The B2 domain of VIVIPAROUS1 is bi-functional and regulates nuclear localization and transactivation. Planta 225, 863-872.

McCarty, D. R., Hattori, T., Carson, C. B., Vasil, V., Lazar, M., and Vasil, I. K. (1991). The Viviparous-1 developmental gene of maize encodes a novel transcriptional activator. Cell 66, 895-905.

Miki, D., and Shimamoto, K. (2004). Simple RNAi vectors for stable and transient suppression of gene function in rice. Plant Cell Physiol 45, 490-495.

Nakamura, S., Lynch, T. J., and Finkelstein, R. R. (2001). Physical interactions between ABA response loci of Arabidopsis. Plant J 26, 627-635.

Nishimura, N., Sarkeshik, A., Nito, K., Park, S. Y., Wang, A., Carvalho, P. C., Lee, S., Caddell, D. F., Cutler, S. R., Chory, J., Yates, J. R., and Schroeder, J. I. (2009). PYR/PYL/RCAR family members are major in-vivo ABI1 protein phosphatase 2C-interacting proteins in Arabidopsis. Plant J.

Razem, F. A., El-Kereamy, A., Abrams, S. R., and Hill, R. D. (2006). The RNA-binding protein FCA is an abscisic acid receptor. Nature 439, 290-294.

Razem, F. A., El-Kereamy, A., Abrams, S. R., and Hill, R. D. (2008). Retraction. The RNA-binding protein FCA is an abscisic acid receptor. Nature 456, 824.

Shen, Q., Uknes, S. J., and Ho, T. H. (1993). Hormone response complex in a novel abscisic acid and cycloheximide-inducible barley gene. The Journal of biological chemistry 268, 23652-23660.

Simpson, G. G., Dijkwel, P. P., Quesada, V., Henderson, I., and Dean, C. (2003). FY is an RNA 3' end-processing factor that interacts with FCA to control the Arabidopsis floral transition. Cell 113, 777-787.

Suzuki, M., Kao, C. Y., and McCarty, D. R. (1997). The conserved B3 domain of VIVIPAROUS1 has a cooperative DNA binding activity. Plant Cell 9, 799-807.

Takai, K., Soejima, T., Suzuki, T., and Kawazu, K. (2001). Development of a water-soluble preparation of emamectin benzoate and its preventative effect against the wilting of pot-grown pine trees inoculated with the pine wood nematode, Bursaphelenchus xylophilus. Pest management science 57, 463-466.

What is claimed is:

1. A method for inhibition of pre-harvest sprouting in monocot plant seeds, comprising
    (i) introducing a recombinant polynucleotide encoding a FCA protein into a monocot plant cell to obtain a transformed monocot plant cell, wherein the FCA protein comprises an amino acid sequence selected from the group consisting of SEQ ID NO: 1, 2 and 3;
    (ii) producing a transformed monocot plant from said transformed monocot plant cell, wherein the FCA protein is overexpressed in the transformed monocot plant; and
    (iii) selecting a transformed monocot plant that produces plant seeds having a reduced level of pre-harvest sprouting as compared to a non-transgenic monocot plant, which is of the same species as the transformed monocot plant and not introduced with the recombinant polynucleotide encoding the FCA protein.

2. The method of claim 1, wherein the FCA protein comprises the amino acid sequence of SEQ ID NO: 1.

3. The method of claim 1, wherein the FCA protein comprises the amino acid sequence of SEQ ID NO: 2.

4. The method of claim 1, wherein the FCA protein comprises the amino acid sequence of SEQ ID NO: 3.

5. The method of claim 1, wherein the transformed monocot plant is selected from the group consisting of rice, barley, wheat, rye, oat, corn, bamboo, sugar cane, onion, leek and ginger.

6. The method of claim 1, wherein the transformed monocot plant is rice, barley or wheat.

7. The method of claim 1, further comprising (iv) collecting the plant seeds from the transformed monocot plant selected in step (iii).

8. A transgenic monocot plant transformed with a recombinant polynucleotide encoding a FCA protein, which comprises an amino acid sequence selected from the group consisting of SEQ ID NO: 1, 2 and 3, wherein the FCA protein is overexpressed in the transgenic monocot plant, and wherein the transgenic monocot plant produces plant seeds having a reduced level of pre-harvest sprouting as compared to a non-transgenic monocot plant, which is of the same species as the transgenic monocot plant and not introduced with the recombinant polynucleotide encoding the FCA protein.

9. The transgenic monocot plant of claim 8, wherein the transgenic monocot plant is selected from the group consisting of rice, barley, wheat, rye, oat, corn, bamboo, sugar cane, onion, leek, and ginger.

10. The transgenic monocot plant of claim 8, wherein the transgenic monocot plant is selected from the group consisting of rice, barley, wheat, and corn.

* * * * *

```
SEQUENCE LISTING

<160> NUMBER OF SEQ ID NOS: 15

<210> SEQ ID NO 1
<211> LENGTH: 738
<212> TYPE: PRT
<213> ORGANISM: Oryza sativa

<400> SEQUENCE: 1

Met His Arg Gly Gly Asp Arg Ser Thr Asp Pro Ser Ser Gly Pro Ala
1               5                   10                  15

Pro Gly Ser Arg Gly Gly Asp Gly Arg Phe Gly Arg Gly Pro Ser
            20                  25                  30

Arg Trp Ser Ser Gly Gly Gly Gly Gly Ser Gly Ser Pro Pro His
        35                  40                  45

Arg Phe Ser Arg Gly Gly Gly Gly Gly Asp Gly Gly Gly
    50                  55                  60

Gly Gly Gly Gly Gly Arg Phe His Pro Tyr Arg Gly Pro Ser Asp His
65                  70                  75                  80

Ser Gly Gly Gly Gly Tyr Arg Ser Gly Gly Gly Glu Tyr Gly Glu
                85                  90                  95

Pro Gly Ser Gly Pro Arg His Arg Tyr Gly Ser Gly Arg Gly Asp His
            100                 105                 110

Ser Asp His Asp Asn Arg Asn Asn Tyr Val Lys Leu Phe Ile Gly Ser
        115                 120                 125

Val Pro Arg Thr Ala Thr Glu Asp Asp Val Arg Pro Leu Phe Glu Glu
    130                 135                 140

His Gly Asp Val Val Glu Val Ala Leu Ile Lys Asp Arg Lys Thr Gly
145                 150                 155                 160

Glu Gln Gln Gly Cys Cys Phe Val Lys Tyr Ala Thr Ser Glu Glu Ala
                165                 170                 175
```

-continued

```
Glu Arg Ala Ile Arg Ala Leu His Asn Gln Tyr Thr Leu Pro Gly Ala
            180                 185                 190

Met Gly Pro Ile Gln Val Arg Tyr Ala Asp Gly Glu Arg Glu Arg His
        195                 200                 205

Gly Ala Ile Glu His Lys Leu Phe Val Ala Ser Leu Asn Lys Gln Ala
    210                 215                 220

Thr Ala Lys Glu Ile Glu Glu Ile Phe Ala Pro Tyr Gly His Val Glu
225                 230                 235                 240

Asp Val Tyr Ile Met Lys Asp Gly Met Arg Gln Ser Arg Gly Cys Gly
                245                 250                 255

Phe Val Lys Phe Ser Ser Arg Glu Pro Ala Leu Ala Ala Met Ser Ala
            260                 265                 270

Leu Ser Gly Asn Tyr Val Met Arg Gly Cys Glu Gln Pro Leu Ile Ile
        275                 280                 285

Arg Phe Ala Asp Pro Lys Arg Pro Arg Pro Gly Gly Ser Arg Gly Gly
    290                 295                 300

Pro Ala Phe Gly Gly Pro Gly Phe Ser Pro Arg Ser Asp Ala Ala Leu
305                 310                 315                 320

Val Ile Arg Pro Thr Ala Asn Leu Asp Glu Pro Arg Gly Arg His Met
                325                 330                 335

Pro Pro Asp Ser Trp His Pro Ser Ser Pro Arg Ser Ala Pro His Gln
            340                 345                 350

Phe Asn Asn Phe Gly Ser Asp Asn Pro Met Ala Pro Lys Gly Ser Thr
        355                 360                 365

Val Thr Ser Thr Thr Asp Thr Ala Thr Phe Arg Pro Gln Met Phe Ser
    370                 375                 380

Gly Asn Gly Ser Leu Ser Ser Gln Thr Ala Val Pro Ser Ser His
385                 390                 395                 400

Met Gly Met Asn Pro Pro Met Ala Gln Gly His His Leu Gly Gly
                405                 410                 415

Gln Gln Ile Pro Pro Leu Gln Lys Leu Pro Gly Leu Pro Gln Asn Phe
            420                 425                 430

Pro Val Gln Leu Gln Asn Asn Gln Leu Gly Gln Pro Leu Gln Gly Pro
        435                 440                 445

Ala Gln Gln Ile Gly Gln Leu Gln Val Pro Gln Ser Met Gly Pro Gly
    450                 455                 460

Ser Phe Gly Gln Asn Arg Leu Ser Gly Gln Leu Pro Val Ser Gln Pro
465                 470                 475                 480

Leu Met Gln Gln Asn Ala Ser Val Ser Ala Val Gln Val Pro Ser Ala
                485                 490                 495

Val Ser Asn Ser Met Gln Ala Ile Pro Gly Gln Gln His Leu Pro Ser
            500                 505                 510

Asn Val Ala Pro Gln Met Leu Gln Gln Pro Val Gln Met Pro Ser
        515                 520                 525

Gln Ala Pro Gln Leu Leu Leu Gln Gln Ala Ala Leu Gln Ser Ser
    530                 535                 540

Tyr Gln Ser Ser Gln Gln Ala Ile Tyr Gln Leu Gln Gln Leu Gln
545                 550                 555                 560

Leu Met Gln Gln Gln Gln Ser Asn Leu Asn His Gln Pro Thr
                565                 570                 575

Gln Gly Gln Pro Val Gln Ser Ser Asn Pro Gly Ala Pro Asn Ala Ile
            580                 585                 590

Ile Pro Ser Asn Ile Asn Thr Ile Pro Gln Gln Ala Thr Ser Pro Ala
```

```
                    595                 600                 605
Val Pro Leu Thr Cys Asn Trp Thr Glu His Thr Ser Pro Glu Gly Phe
610                 615                 620

Lys Tyr Tyr Tyr Asn Ser Ile Thr Arg Glu Ser Lys Trp Asp Lys Pro
625                 630                 635                 640

Glu Glu Tyr Val Leu Tyr Glu Gln Gln Gln Gln Gln Gln Gln Gln Gln
                645                 650                 655

Lys Leu Leu Leu Leu Gln Gln His Lys Gln Lys Leu Ala Met Gln Gln
                660                 665                 670

Leu Gln Ser Pro Pro Gln Ala Gln Thr His Pro Ala Met Gln Pro Val
                675                 680                 685

Gln Gln Ile Pro Gln Ala Gln Gln Gly Gln Gln Met Gln Met Lys
690                 695                 700

Gln Gln Glu Leu Asn Tyr Thr Gln Leu Gln Thr Pro Gly Ala Ile Asp
705                 710                 715                 720

Pro Ser Arg Ile Gln Gln Gly Ile Gln Ser Ala Gln Glu Arg Ala Trp
                725                 730                 735

Lys Ser

<210> SEQ ID NO 2
<211> LENGTH: 743
<212> TYPE: PRT
<213> ORGANISM: Hordeum vulgare

<400> SEQUENCE: 2

Met His Arg Gly Ser Asp Arg Ser Ala Asp Pro Ser Gly Pro Ala Gly
1               5                   10                  15

Ala Ala Arg Ser Gly Gly Asp Gly Arg Phe Ala Arg Gly Pro Ser Arg
                20                  25                  30

Trp Ser Gly Gly Gly Gly Ser Pro Pro His Arg Ser Ser Arg
                35                  40                  45

Gly Gly Ser Ser Asp Gly Gly Gly Gly Gly Gly Gly Gly Gly
                50                  55                  60

Arg Leu His Pro Tyr Arg Ala Pro Ser Glu Tyr Val Val Gly Gly
65              70                  75                  80

Gly Thr Gly Gly Tyr Arg Gly Gly Gly Asp Phe Asp Glu Thr Ala
                85                  90                  95

Gly Gly Ala Lys Ser Arg Tyr Gly Gly Gly Gly Gly Gly Arg Gly
                100                 105                 110

Asp Tyr Ser Asp His Asp Asn Lys Ser Gly Tyr Val Lys Leu Phe Val
                115                 120                 125

Gly Ser Val Pro Arg Thr Ala Asn Glu Asp Asp Val Arg Pro Leu Phe
130                 135                 140

Glu Asp His Gly Asp Val Leu Glu Val Ala Leu Ile Arg Asp Arg Lys
145                 150                 155                 160

Thr Gly Glu Gln Gln Gly Cys Cys Phe Val Lys Tyr Ala Thr Ser Glu
                165                 170                 175

Glu Ala Glu Arg Ala Ile Arg Ala Leu His Asn Gln Cys Thr Ile Pro
                180                 185                 190

Gly Ala Met Gly Pro Val Gln Val Arg Tyr Ala Asp Gly Glu Lys Glu
                195                 200                 205

Arg His Gly Ser Ile Glu His Lys Leu Phe Val Ala Ser Leu Asn Lys
                210                 215                 220

Gln Ala Thr Ala Lys Glu Ile Glu Glu Ile Phe Ala Pro Phe Gly His
```

-continued

```
            225                 230                 235                 240
Val Glu Asp Val Tyr Ile Met Lys Asp Gly Met Arg Gln Ser Arg Gly
                    245                 250                 255

Cys Gly Phe Val Lys Phe Ser Ser Lys Glu Pro Ala Leu Ala Ala Met
                    260                 265                 270

Asn Ser Leu Ser Gly Thr Tyr Ile Met Arg Gly Cys Glu Gln Pro Leu
                275                 280                 285

Ile Val Arg Phe Ala Asn Pro Lys Arg Pro Arg Pro Gly Glu Ser Arg
            290                 295                 300

Gly Gly Pro Ala Phe Gly Pro Gly Val Ser Arg Ser Asp Ala
305                 310                 315                 320

Ala Leu Val Ile Arg Pro Thr Ala Asn Leu Asp Glu Gln Ile Gly Arg
                325                 330                 335

His Met Pro Pro Asp Thr Trp Arg Pro Ser Ser Pro Ser Met Ala
                340                 345                 350

Pro His Gln Phe Asn Asn Phe Gly Ser Asp Asn Ser Met Gly Leu Met
                355                 360                 365

Gly Gly Pro Val Thr Ser Ala Ala Asp Asn Val Ala Phe Arg Pro Gln
        370                 375                 380

Leu Phe His Gly Asn Gly Ser Leu Ser Ser Gln Thr Ala Val Pro Ala
385                 390                 395                 400

Ser Ser His Met Gly Ile Asn Pro Ser Leu Ser Gln Gly His His Leu
                    405                 410                 415

Gly Gly Pro Gln Ile Pro Pro Leu Gln Lys Pro Thr Gly Leu Gln Gln
                420                 425                 430

Asn Phe Pro Val Gln Leu Gln Asn Ala Gln Gln Gly Gln Leu His Ala
                435                 440                 445

Ser Gln Ser Leu Gly Pro Gly Ser Phe Gly Gln Asn Ile Pro Thr Met
        450                 455                 460

Gln Leu Pro Gly Gln Leu Pro Val Ser Gln Pro Leu Thr Gln Asn
465                 470                 475                 480

Ala Ser Ala Cys Ala Leu Gln Ala Pro Ser Ala Val Gln Ser Asn Pro
                    485                 490                 495

Met Gln Ser Val Pro Gly Gln Gln Leu Pro Ser Asn Leu Thr Pro
                500                 505                 510

Gln Met Leu Gln Gln Pro Val Gln Gln Met Leu Ser Gln Ala Pro Gln
                515                 520                 525

Leu Leu Leu Gln Gln Gln Ala Ala Met Gln Ser Ser Tyr Gln Ser
        530                 535                 540

Ser Gln Gln Thr Ile Phe Gln Leu Gln Gln Leu Gln Leu Met Gln
545                 550                 555                 560

Gln Gln Gln His Gln Gln Pro Asn Leu Asn Gln Pro His Thr
                    565                 570                 575

Gln Val Pro Lys Gln Gly Gln Pro Val Gln Ser Asn Ala Pro Gly
                580                 585                 590

Ala Pro Ala Ala Met Met Thr Thr Asn Ile Asn Ala Ile Pro Gln Gln
                595                 600                 605

Val Asn Ser Pro Ala Val Ser Leu Thr Cys Asn Trp Thr Glu His Thr
                610                 615                 620

Ser Pro Glu Gly Phe Lys Tyr Tyr Asn Ser Ile Thr Arg Glu Ser
625                 630                 635                 640

Lys Trp Glu Lys Pro Glu Glu Tyr Val Leu Tyr Glu Gln Gln Gln Gln
                    645                 650                 655
```

```
Gln Gln Gln His Gln Lys Leu Ile Leu Leu Gln Gln His Gln Lys
                660             665                 670
Leu Val Ala Gln Gln Leu Gln Ser Pro Pro Gln Ala Gln Thr Ile Pro
        675                 680                 685
Ser Met Gln Ser Met Gln His His Pro Gln Ser Gln Gln Gly His Asn
    690                 695                 700
Gln Met Gln Met Lys Gln Gln Asp Leu Asn Tyr Asn Gln Leu Gln Pro
705                 710                 715                 720
Thr Gly Thr Ile Asp Pro Ser Arg Ile Gln Gln Gly Ile Gln Ala Ala
                725                 730                 735
Gln Glu Arg Ser Trp Lys Ser
                740

<210> SEQ ID NO 3
<211> LENGTH: 735
<212> TYPE: PRT
<213> ORGANISM: Triticum aestivum

<400> SEQUENCE: 3

Arg Ser Gly Asp Pro Ser Gly Pro Ala Gly Gly Ala Arg Ser Gly Ala
1               5                   10                  15
Asp Gly Arg Phe Ala Arg Gly Pro Ser Arg Trp Ser Gly Gly Gly Gly
                20                  25                  30
Gly Ser Pro Pro His Arg Ser Arg Gly Gly Ser Ser Asp Gly
            35                  40                  45
Gly Gly Gly Gly Gly Arg Phe His Pro Tyr Arg Ala Pro Ser Glu
    50                  55                  60
Tyr Val Gly Gly Gly Gly Thr Gly Tyr Arg Gly Gly Gly Gly
65                  70                  75                  80
Gly Gly Asp Phe Gly Glu Thr Ala Gly Ala Arg Ser Arg Tyr Gly
                85                  90                  95
Gly Gly Gly Ser Gly Gly Gly Gly Arg Gly Asp Cys Ser Asp His Asp
            100                 105                 110
Asn Lys Ser Gly Tyr Val Lys Leu Phe Val Gly Ser Val Pro Arg Thr
        115                 120                 125
Ala Asn Glu Asp Asp Val Arg Pro Leu Phe Glu Asp His Gly Asp Val
    130                 135                 140
Leu Glu Val Ala Leu Ile Arg Asp Arg Lys Thr Gly Glu Gln Gln Gly
145                 150                 155                 160
Cys Cys Phe Val Lys Tyr Ala Thr Ser Glu Glu Ala Glu Arg Ala Ile
                165                 170                 175
Arg Ala Leu His Asn Gln Cys Thr Ile Pro Gly Ala Met Gly Pro Val
            180                 185                 190
Gln Val Arg Tyr Ala Asp Gly Glu Lys Glu Arg His Gly Ser Ile Glu
        195                 200                 205
Tyr Lys Leu Phe Val Ala Ser Leu Asn Lys Gln Ala Thr Ala Lys Glu
    210                 215                 220
Ile Glu Glu Ile Phe Ala Pro Phe Gly His Val Glu Asp Val Tyr Ile
225                 230                 235                 240
Met Lys Asp Gly Met Arg Gln Ser Arg Gly Cys Gly Phe Val Lys Phe
                245                 250                 255
Ser Ser Lys Glu Pro Ala Leu Ala Ala Met Asn Ser Leu Ser Gly Thr
            260                 265                 270
Tyr Ile Met Arg Gly Cys Glu Gln Pro Leu Ile Val Arg Phe Ala Asp
```

```
                275                 280                 285
Pro Lys Arg Pro Arg Pro Gly Glu Ser Arg Gly Pro Ala Phe Gly
    290                 295                 300
Gly Pro Gly Val Ser Ser Arg Ser Asp Ala Ala Leu Val Ile Arg Pro
305                 310                 315                 320
Thr Ala Asn Leu Asp Glu Gln Ile Gly Arg His Met Pro Pro Asp Ser
                325                 330                 335
Trp Arg Pro Ser Ser Pro Ser Ser Met Ala Pro His Gln Phe Asn Asn
                340                 345                 350
Phe Gly Ser Asp Asn Ser Met Gly Leu Met Gly Gly Pro Val Thr Ser
                355                 360                 365
Ala Ala Asp Asn Val Thr Phe Arg Pro Gln Met Phe His Gly Asn Gly
            370                 375                 380
Ser Leu Ser Ser Gln Thr Ala Val Pro Thr Ser Ser His Met Gly Ile
385                 390                 395                 400
Asn Pro Ser Leu Ser Gln Gly His His Leu Gly Gly Pro Gln Ile Ser
                405                 410                 415
Pro Leu Gln Lys Pro Thr Gly Gln Pro Gln Asn Phe Pro Val Gln Leu
                420                 425                 430
Gln Asn Ala Gln Gln Gly Leu His Ala Ser Gln Ser Leu Gly Pro
                435                 440                 445
Gly Ser Phe Gly Gln Asn Ile Pro Thr Met Gln Leu Pro Gly Gln Leu
    450                 455                 460
Pro Val Ser Gln Pro Leu Thr Gln Gln Asn Ala Ser Ala Gly Ala Leu
465                 470                 475                 480
Gln Ala Pro Ser Ala Val Gln Ser Asn Pro Ile Gln Ala Val Pro Gly
                485                 490                 495
Gln Gln Gln Leu Pro Ser Asn Val Thr Pro Gln Met Leu Gln Gln Pro
                500                 505                 510
Val Gln Gln Met Leu Ser Gln Ala Pro Gln Leu Leu Leu Gln Gln Gln
            515                 520                 525
Gln Ala Ala Ile Gln Ser Ser Tyr Gln Ser Ser Gln Gln Thr Ile Phe
            530                 535                 540
Gln Leu Gln Gln Gln Leu Gln Leu Leu Gln Gln Gln Gln His Gln
545                 550                 555                 560
Gln Gln Pro Asn Leu Asn Gln Gln Pro His Thr Gln Val Pro Lys Gln
                565                 570                 575
Gln Gly Gln Pro Val Gln Ser Asn Thr Pro Gly Ala Pro Ala Ala Met
                580                 585                 590
Met Thr Thr Lys Ile Asn Ala Ile Pro Gln Gln Val Asn Ser Pro Ala
            595                 600                 605
Val Ser Leu Thr Cys Asn Trp Thr Glu His Thr Ser Pro Glu Gly Phe
    610                 615                 620
Lys Tyr Tyr Tyr Asn Ser Ile Thr Arg Glu Ser Lys Trp Glu Lys Pro
625                 630                 635                 640
Glu Glu Tyr Ile Leu Tyr Glu Gln Gln Gln His Gln Lys Leu Ile
                645                 650                 655
Leu Leu Gln Gln His Gln Lys Leu Val Ala Gln Gln Leu Gln Ser
            660                 665                 670
Pro Pro Gln Ala Gln Thr Ile Pro Pro Met Gln Ser Met Gln His His
            675                 680                 685
Pro Gln Ser Gln Gln Gly His Asn Gln Met Gln Met Lys Gln Gln Asp
            690                 695                 700
```

```
Leu Asn Tyr Asn Gln Leu Gln Ala Thr Gly Thr Ile Asp Pro Ser Arg
705                 710                 715                 720

Ile Gln Gln Gly Ile Gln Ala Ala Gln Glu Arg Ser Trp Lys Ser
                725                 730                 735

<210> SEQ ID NO 4
<211> LENGTH: 80
<212> TYPE: PRT
<213> ORGANISM: Artificial Sequence
<220> FEATURE:
<223> OTHER INFORMATION: RRM1 consensus sequence
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: misc_feature
<222> LOCATION: (12)..(12)
<223> OTHER INFORMATION: Xaa can be any naturally occurring amino acid
<220> FEATURE:
<221> NAME/KEY: misc_feature
<222> LOCATION: (22)..(22)
<223> OTHER INFORMATION: Xaa can be any naturally occurring amino acid
<220> FEATURE:
<221> NAME/KEY: misc_feature
<222> LOCATION: (27)..(27)
<223> OTHER INFORMATION: Xaa can be any naturally occurring amino acid
<220> FEATURE:
<221> NAME/KEY: misc_feature
<222> LOCATION: (33)..(33)
<223> OTHER INFORMATION: Xaa can be any naturally occurring amino acid
<220> FEATURE:
<221> NAME/KEY: misc_feature
<222> LOCATION: (65)..(65)
<223> OTHER INFORMATION: Xaa can be any naturally occurring amino acid
<220> FEATURE:
<221> NAME/KEY: misc_feature
<222> LOCATION: (67)..(67)
<223> OTHER INFORMATION: Xaa can be any naturally occurring amino acid
<220> FEATURE:
<221> NAME/KEY: misc_feature
<222> LOCATION: (74)..(74)
<223> OTHER INFORMATION: Xaa can be any naturally occurring amino acid

<400> SEQUENCE: 4

Lys Leu Phe Xaa Gly Ser Val Pro Arg Thr Ala Xaa Glu Asp Asp Val
1               5                   10                  15

Arg Pro Leu Phe Glu Xaa His Gly Asp Val Xaa Glu Val Ala Leu Ile
                20                  25                  30

Xaa Asp Arg Lys Thr Gly Glu Gln Gln Gly Cys Cys Phe Val Lys Tyr
            35                  40                  45

Ala Thr Ser Glu Glu Ala Glu Arg Ala Ile Arg Ala Leu His Asn Gln
    50                  55                  60

Xaa Thr Xaa Pro Gly Ala Met Gly Pro Xaa Gln Val Arg Tyr Ala Asp
65                  70                  75                  80

<210> SEQ ID NO 5
<211> LENGTH: 79
<212> TYPE: PRT
<213> ORGANISM: Artificial sequence
<220> FEATURE:
<223> OTHER INFORMATION: RRM2 consensue sequence
<220> FEATURE:
<221> NAME/KEY: misc_feature
<222> LOCATION: (23)..(23)
<223> OTHER INFORMATION: Xaa can be any naturally occurring amino acid
<220> FEATURE:
<221> NAME/KEY: misc_feature
<222> LOCATION: (50)..(50)
<223> OTHER INFORMATION: Xaa can be any naturally occurring amino acid
```

```
<220> FEATURE:
<221> NAME/KEY: misc_feature
<222> LOCATION: (58)..(59)
<223> OTHER INFORMATION: Xaa can be any naturally occurring amino acid
<220> FEATURE:
<221> NAME/KEY: misc_feature
<222> LOCATION: (63)..(63)
<223> OTHER INFORMATION: Xaa can be any naturally occurring amino acid
<220> FEATURE:
<221> NAME/KEY: misc_feature
<222> LOCATION: (65)..(65)
<223> OTHER INFORMATION: Xaa can be any naturally occurring amino acid
<220> FEATURE:
<221> NAME/KEY: misc_feature
<222> LOCATION: (75)..(75)
<223> OTHER INFORMATION: Xaa can be any naturally occurring amino acid
<220> FEATURE:
<221> NAME/KEY: misc_feature
<222> LOCATION: (79)..(79)
<223> OTHER INFORMATION: Xaa can be any naturally occurring amino acid

<400> SEQUENCE: 5

Lys Leu Phe Val Ala Ser Leu Asn Lys Gln Ala Thr Ala Lys Glu Ile
1               5                   10                  15

Glu Glu Ile Phe Ala Pro Xaa Gly His Val Glu Asp Val Tyr Ile Met
            20                  25                  30

Lys Asp Gly Met Arg Gln Ser Arg Gly Cys Gly Phe Val Lys Phe Ser
        35                  40                  45

Ser Xaa Glu Pro Ala Leu Ala Ala Met Xaa Xaa Leu Ser Gly Xaa Tyr
    50                  55                  60

Xaa Met Arg Gly Cys Glu Gln Pro Leu Ile Xaa Arg Phe Ala Xaa
65                  70                  75

<210> SEQ ID NO 6
<211> LENGTH: 43
<212> TYPE: PRT
<213> ORGANISM: Artificial Sequence
<220> FEATURE:
<223> OTHER INFORMATION: WW consensue sequence
<220> FEATURE:
<221> NAME/KEY: misc_feature
<222> LOCATION: (1)..(2)
<223> OTHER INFORMATION: Xaa can be any naturally occurring amino acid
<220> FEATURE:
<221> NAME/KEY: misc_feature
<222> LOCATION: (7)..(7)
<223> OTHER INFORMATION: Xaa can be any naturally occurring amino acid
<220> FEATURE:
<221> NAME/KEY: misc_feature
<222> LOCATION: (35)..(35)
<223> OTHER INFORMATION: Xaa can be any naturally occurring amino acid
<220> FEATURE:
<221> NAME/KEY: misc_feature
<222> LOCATION: (41)..(41)
<223> OTHER INFORMATION: Xaa can be any naturally occurring amino acid

<400> SEQUENCE: 6

Xaa Xaa Ser Pro Ala Val Xaa Leu Thr Cys Asn Trp Thr Glu His Thr
1               5                   10                  15

Ser Pro Glu Gly Phe Lys Tyr Tyr Tyr Asn Ser Ile Thr Arg Glu Ser
            20                  25                  30

Lys Trp Xaa Lys Pro Glu Glu Tyr Xaa Leu Tyr
        35                  40

<210> SEQ ID NO 7
<211> LENGTH: 80
<212> TYPE: PRT
<213> ORGANISM: Oryza sativa
```

```
<400> SEQUENCE: 7

Lys Leu Phe Ile Gly Ser Val Pro Arg Thr Ala Thr Glu Asp Asp Val
1               5                   10                  15

Arg Pro Leu Phe Glu Glu His Gly Asp Val Val Glu Val Ala Leu Ile
            20                  25                  30

Lys Asp Arg Lys Thr Gly Glu Gln Gln Gly Cys Cys Phe Val Lys Tyr
        35                  40                  45

Ala Thr Ser Glu Glu Ala Glu Arg Ala Ile Arg Ala Leu His Asn Gln
    50                  55                  60

Tyr Thr Leu Pro Gly Ala Met Gly Pro Ile Gln Val Arg Tyr Ala Asp
65                  70                  75                  80

<210> SEQ ID NO 8
<211> LENGTH: 79
<212> TYPE: PRT
<213> ORGANISM: Oryza sativa

<400> SEQUENCE: 8

Lys Leu Phe Val Ala Ser Leu Asn Lys Gln Ala Thr Ala Lys Glu Ile
1               5                   10                  15

Glu Glu Ile Phe Ala Pro Tyr Gly His Val Glu Asp Val Tyr Ile Met
            20                  25                  30

Lys Asp Gly Met Arg Gln Ser Arg Gly Cys Gly Phe Val Lys Phe Ser
        35                  40                  45

Ser Arg Glu Pro Ala Leu Ala Ala Met Ser Ala Leu Ser Gly Asn Tyr
    50                  55                  60

Val Met Arg Gly Cys Glu Gln Pro Leu Ile Ile Arg Phe Ala Asp
65                  70                  75

<210> SEQ ID NO 9
<211> LENGTH: 43
<212> TYPE: PRT
<213> ORGANISM: Oryza sativa

<400> SEQUENCE: 9

Ala Thr Ser Pro Ala Val Pro Leu Thr Cys Asn Trp Thr Glu His Thr
1               5                   10                  15

Ser Pro Glu Gly Phe Lys Tyr Tyr Tyr Asn Ser Ile Thr Arg Glu Ser
            20                  25                  30

Lys Trp Asp Lys Pro Glu Glu Val Leu Tyr
        35                  40

<210> SEQ ID NO 10
<211> LENGTH: 80
<212> TYPE: PRT
<213> ORGANISM: Hordeum vulgare

<400> SEQUENCE: 10

Lys Leu Phe Val Gly Ser Val Pro Arg Thr Ala Asn Glu Asp Asp Val
1               5                   10                  15

Arg Pro Leu Phe Glu Asp His Gly Asp Val Leu Glu Val Ala Leu Ile
            20                  25                  30

Arg Asp Arg Lys Thr Gly Glu Gln Gln Gly Cys Cys Phe Val Lys Tyr
        35                  40                  45

Ala Thr Ser Glu Glu Ala Glu Arg Ala Ile Arg Ala Leu His Asn Gln
    50                  55                  60

Cys Thr Ile Pro Gly Ala Met Gly Pro Val Gln Val Arg Tyr Ala Asp
65                  70                  75                  80
```

<210> SEQ ID NO 11
<211> LENGTH: 79
<212> TYPE: PRT
<213> ORGANISM: Hordeum vulgare

<400> SEQUENCE: 11

Lys Leu Phe Val Ala Ser Leu Asn Lys Gln Ala Thr Ala Lys Glu Ile
1               5                   10                  15

Glu Glu Ile Phe Ala Pro Phe Gly His Val Glu Asp Val Tyr Ile Met
            20                  25                  30

Lys Asp Gly Met Arg Gln Ser Arg Gly Cys Gly Phe Val Lys Phe Ser
        35                  40                  45

Ser Lys Glu Pro Ala Leu Ala Ala Met Asn Ser Leu Ser Gly Thr Tyr
    50                  55                  60

Ile Met Arg Gly Cys Glu Gln Pro Leu Ile Val Arg Phe Ala Asn
65                  70                  75

<210> SEQ ID NO 12
<211> LENGTH: 43
<212> TYPE: PRT
<213> ORGANISM: Hordeum vulgare

<400> SEQUENCE: 12

Val Asn Ser Pro Ala Val Ser Leu Thr Cys Asn Trp Thr Glu His Thr
1               5                   10                  15

Ser Pro Glu Gly Phe Lys Tyr Tyr Asn Ser Ile Thr Arg Glu Ser
            20                  25                  30

Lys Trp Glu Lys Pro Glu Glu Tyr Val Leu Tyr
        35                  40

<210> SEQ ID NO 13
<211> LENGTH: 80
<212> TYPE: PRT
<213> ORGANISM: Triticum aestivum

<400> SEQUENCE: 13

Lys Leu Phe Val Gly Ser Val Pro Arg Thr Ala Asn Glu Asp Asp Val
1               5                   10                  15

Arg Pro Leu Phe Glu Asp His Gly Asp Val Leu Glu Val Ala Leu Ile
            20                  25                  30

Arg Asp Arg Lys Thr Gly Glu Gln Gln Gly Cys Cys Phe Val Lys Tyr
        35                  40                  45

Ala Thr Ser Glu Glu Ala Glu Arg Ala Ile Arg Ala Leu His Asn Gln
    50                  55                  60

Cys Thr Ile Pro Gly Ala Met Gly Pro Val Gln Val Arg Tyr Ala Asp
65                  70                  75                  80

<210> SEQ ID NO 14
<211> LENGTH: 79
<212> TYPE: PRT
<213> ORGANISM: Triticum aestivum

<400> SEQUENCE: 14

Lys Leu Phe Val Ala Ser Leu Asn Lys Gln Ala Thr Ala Lys Glu Ile
1               5                   10                  15

Glu Glu Ile Phe Ala Pro Phe Gly His Val Glu Asp Val Tyr Ile Met
            20                  25                  30

Lys Asp Gly Met Arg Gln Ser Arg Gly Cys Gly Phe Val Lys Phe Ser

```
                      35             40               45
Ser Lys Glu Pro Ala Leu Ala Ala Met Asn Ser Leu Ser Gly Thr Tyr
 50                 55              60

Ile Met Arg Gly Cys Glu Gln Pro Leu Ile Val Arg Phe Ala Asp
                 65              70              75

<210> SEQ ID NO 15
<211> LENGTH: 43
<212> TYPE: PRT
<213> ORGANISM: Triticum aestivum

<400> SEQUENCE: 15

Val Asn Ser Pro Ala Val Ser Leu Thr Cys Asn Trp Thr Glu His Thr
 1               5                  10                  15

Ser Pro Glu Gly Phe Lys Tyr Tyr Asn Ser Ile Thr Arg Glu Ser
                20              25                  30

Lys Trp Glu Lys Pro Glu Glu Tyr Ile Leu Tyr
             35              40
```